United States Patent [19]

St. Geme, III et al.

[11] Patent Number: 6,060,059
[45] Date of Patent: May 9, 2000

[54] HAEMOPHILUS ADHESION PROTEINS

[75] Inventors: Joseph W. St. Geme, III, St. Louis; Stephen J. Barenkamp, Webster Groves, both of Mo.

[73] Assignees: Washington University; St. Louis University, both of St. Louis, Mo.

[21] Appl. No.: 08/685,467

[22] Filed: Jul. 24, 1996

Related U.S. Application Data

[62] Division of application No. 08/409,995, Mar. 24, 1995, Pat. No. 5,646,259.

[51] Int. Cl.$^7$ .................................................. A61K 39/02
[52] U.S. Cl. .................................. 424/190.1; 424/185.1; 424/256.1; 530/350
[58] Field of Search ............................. 424/256.1, 185.1, 424/190.1; 530/350; 536/23.1, 23.7; 435/69.1, 172.1

[56] References Cited

FOREIGN PATENT DOCUMENTS

| | | |
|---|---|---|
| 92/10936 | 7/1992 | WIPO . |
| 94/00149 | 1/1994 | WIPO . |
| 96/02648 | 2/1996 | WIPO . |

OTHER PUBLICATIONS

Sirakova, T., et al., "Role of Fimbriae Expressed by Nontypeable *Haemophilus influenzae* in Pathogenesis of and Protection against Otitis Media and Relatedness of the Fimbrin Subunit to Outer Membrane Protein A," *Infection and Immunity*, 62(5):2002–2020 (1994).

van Ham, S. M., et al., "The Fimbrial Gene Cluster of *Haemophilus influenzae* type b," *Molecular Microbiology*, 3(4):673–684 (1994).

van Ham, S. M., et al., "Contribution of the Major and Minor Subunits to Fimbria-Mediated Adherence of *Haemophilus influenzae* to Human Epithelial Cells and Erythrocytes," *Infection and Imuunity*, 63(12):4883–4889 (1995).

Pichichero, M.E., et al., "Do Pili Play a Role in Pathogenicity of *Haemophilus Influenzae* Type B," *The Lancet*, 960–962 (1982).

Bakaletz, L.O., et al., "Frequency of Fimbriation of Nontypable *Haemophilus influenzae* and its Ability to Adhere to Chinchilla and Human Respiratory Epithelium," *Infection and Immunity*, 56(2):331–335 (1988).

van Ham, S.M., et al., "Cloning and Expression in *Escherichia coli* of *Haemophilus influenzae* Fimbrial Genes Establishes Adherence to Oropharyngeal Epithelial Cells," *The EMBO J.* 8(11):3535–3540 (1989).

Barenkamp, S.J., et al., "Cloning, Expression, and DNA Sequence Analysis of Genes Encoding Nontypeabale *Haemophilus influenzae* High–Molecular–Weight Surface–Exposed Proteins Related to Filamentous Hemagglutinin of *Bordetella pertussis*," *Infection and Immunity*, 60(4):1302–1313 (1992).

St. Geme, J.W., et al., "Surface Structures and Adherence Properties of Diverse Strains of *Haemophilus influenzae* Biogroup aegyptius," *Infection and Immunity*, 59(10):3366–3371 (1991).

St. Geme, J.W., et al., "High–Molucular–Weight Proteins of Nontypable *Haemophilus influenzae* Mediate Attachement to Human Epithelial Cells," *PNAS USA*, 90:2875–2879 (1993).

St. Geme, J.W., et al., "*Haemophilus influenzae* Adheres to and Enters Cultured Human Epithelial Cells," *Infection and Immunity*, 58(12):4036–4044 (1990).

St. Geme, J.W., et al., "Evidence that Surface Fibrils Expressed by *Haemophilus influenzae* type b Promote Attachment to Human Epithelial Cells," *Molecular Microbiology*, 15(1):77–85 (1995).

St. Geme, J.W., et al., "A *Haemophilus influenzae* IgA Protease–Like Protein Promotes Intimate Interaction with Human Epithelial Cells," *Molecular Microbiology*, 14(2):217–233 (1994).

Barenkamp, S.J., et al., "Genes Encoding High–Molecular–Weight Adhesion Proteins of Nontypeable *Haemophilus influenzae* Are Part of Gene Clusters," *Infection and Immunity*, 62(8):3320–3328 (1994).

Barenkamp, S.J., et al., "Identification of a Second Family of High Molecular Weight Adhesion Proteins Expressed by Nontypeable *Haemophilus influenzae* (NTHl)" 105th Annual Meeting of the American Pediatric Society and the 64th Ammual Meeting of the Society for Pediatric Research, San Diego:USA, May 7–11, Abstract No. 1003, *Pediatric Research*, 37 (4 part 2), p. 170A (1995).

Fleischmann, R.D. et al., "Whole–Genome Random Sequencing and Assembly of *Haemophilus influenzae* Rd," *Science*, 269 (5223):496–498, 507–512 (1995).

Barenkamp, S.J., et al., "Identification of a Second Family of High–Molecular–Weight Adhesion Proteins Expressed by Non–Typable *Haemophilus influenzae*,"*Molecular Microbiology*, 19(6):1215–1223 (1996).

*Primary Examiner*—Christopher L. Chin
*Assistant Examiner*—Jennifer Graser
*Attorney, Agent, or Firm*—Flehr Hohbach Test Albritton & Herbert LLP; Richard F. Trecartin; Robin M. Silva

[57] ABSTRACT

The invention relates to novel Haemophilus adhesion proteins, nucleic acids, and antibodies.

4 Claims, 19 Drawing Sheets

```
ATGAACAAAA TTTTTAACGT TATTTGGAAT GTTGTGACTC AAACTTGGGT TGTCGTATCT    60
GAACTCACTC GCACCCACAC CAAATGCGCC TCCGCCACCG TGGCGGTTGC CGTATTGGCA   120
ACCCTGTTGT CCGCAACGGT TGAGGCGAAC AACAATACTC CTGTTACGAA TAAGTTGAAG   180
GCTTATGGCG ATGCGAATTT TAATTTCACT AATAATTCGA TAGCAGATGC AGAAAAACAA   240
GTTCAAGAGG CTTATAAAGG TTTATTAAAT CTAAATGAAA AAAATGCGAG TGATAAACTG   300
TTGGTGGAGG ACAATACTGC GGCGACCGTA GGCAATTTGC GTAAATTGGG CTGGGTATTG   360
TCTAGCAAAA ACGGCACAAG GAACGAGAAA AGCCAACAAG TCAAACATGC GGATGAAGTG   420
TTGTTTGAAG GCAAAGGCGG TGTGCAGGTT ACTTCCACCT CTGAAAACGG CAAACACACC   480
ATTACCTTTG CTTTAGCGAA AGACCTTGGT GTGAAAACTG CGACTGTGAG TGATACCTTA   540
ACGATTGGCG GTGGTGCTGC TGCAGGTGCT ACAACAACAC GAAAGTGAA TGTAACTAGT   600
ACAACTGATG GCTTGAAGTT CGCTAAAGAT GCTGCGGGTG CTAATGGCGA TACTACGGTT   660
CACTTGAATG GTATTGGTTC AACCTTGACA GACACGCTTG TGGGTTCTCC TGCTACTCAT   720
ATTGACGGAG GAGATCAAAG TACGCATTAC ACTCGTGCAG CAAGTATCAA GGATGTCTTG   780
AATGCGGGTT GGAATATCAA GGGTGTTAAA GCTGGCTCAA CAACTGGTCA ATCAGAAAAT   840
GTCGATTTTG TTCATACTTA CGATACTGTT GAGTTCTTGA GTGCGGATAC AGAGACCACG   900
ACTGTTACTG TAGATAGCAA AGAAAACGGT AAGAGAACCG AAGTTAAAAT CGGTGCGAAG   960
ACTTCTGTTA TCAAAGAAAA AGACGGTAAG TTATTTACTG GAAAAGCTAA CAAAGAGACA  1020
AATAAAGTTG ATGGTGCTAA CGCGACTGAA GATGCAGACG AAGGCAAAGG CTTAGTGACT  1080
GCGAAAGATG TGATTGACGC AGTGAATAAG ACTGGTTGGA GAATTAAAAC AACCGATGCT  1140
AATGGTCAAA ATGGCGACTT CGCAACTGTT GCATCAGGCA CAAATGTAAC CTTTGCTAGT  1200
GGTAATGGTA CAACTGCGAC TGTAACTAAT GGCACCGATG GTATTACCGT TAAGTATGAT  1260
GCGAAAGTTG GCGACGGCTT AAAACTAGAT GGCGATAAAA TCGCTGCAGA TACGACCGCA  1320
CTTACTGTGA ATGATGGTAA GAACGCTAAT AATCCGAAAG GTAAAGTGGC TGATGTTGCT  1380
TCAACTGACG AGAAGAAATT GGTTACAGCA AAAGGTTTAG TAACAGCCTT AAACAGTCTA  1440
AGCTGGACTA CAACTGCTGC TGAGGCGGAC GGTGGTACGC TTGATGGAAA TGCAAGTGAG  1500
CAAGAAGTTA AAGCGGGCGA TAAAGTAACC TTTAAAGCAG GCAAGAACTT AAAAGTGAAA  1560
CAAGAGGGTG CGAACTTTAC TTATTCACTG CAAGATGCTT TAACAGGCTT AACGAGCATT  1620
ACTTTAGGTA CAGGAAATAA TGGTGCGAAA ACTGAAATCA ACAAAGACGG CTTAACCATC  1680
ACACCAGCAA ATGGTGCGGG TGCAAATAAT GCAAACACCA TCAGCGTAAC CAAAGACGGC  1740
```

FIG._1A

| | | | | | |
|---|---|---|---|---|---|
| ATTAGTGCGG | GCGGTCAGTC | GGTTAAAAAC | GTTGTGAGCG | GACTGAAGAA | ATTTGGTGAT | 1800 |
| GCGAATTTCG | ATCCGCTGAC | TAGCTCCGCC | GACAACTTAA | CGAAACAAAA | TGACGATGCC | 1860 |
| TATAAAGGCT | TGACCAATTT | GGATGAAAAA | GGTACAGACA | AGCAAACTCC | AGTTGTTGCC | 1920 |
| GACAATACCG | CCGCAACCGT | GGGCGATTTG | CGCGGCTTGG | GCTGGGTCAT | TTCTGCGGAC | 1980 |
| AAAACCACAG | GCGGCTCAAC | GGAATATCAC | GATCAAGTTC | GGAATGCGAA | CGAAGTGAAA | 2040 |
| TTCAAAAGCG | GCAACGGTAT | CAATGTTTCC | GGTAAAACGG | TCAACGGTAG | GCGTGAAATT | 2100 |
| ACTTTTGAAT | TGGCTAAAGG | TGAAGTGGTT | AAATCGAATG | AATTTACCGT | CAAAGAAACC | 2160 |
| AATGGAAAGG | AAACGAGCCT | GGTTAAAGTT | GGCGATAAAT | ATTACAGCAA | AGAGGATATT | 2220 |
| GACTTAACAA | CAGGTCAGCC | TAAATTAAAA | GATGGCAATA | CAGTTGCTGC | GAAATATCAA | 2280 |
| GATAAAGGTG | GCAAAGTCGT | TTCTGTAACG | GATAATACTG | AAGCTACCAT | AACCAACAAA | 2340 |
| GGTTCTGGCT | ATGTAACAGG | TAACCAAGTG | GCAGATGCGA | TTGCGAAATC | AGGCTTTGAG | 2400 |
| CTTGGCTTGG | CTGATGAAGC | TGATGCGAAA | CGGGCGTTTG | ATGATAAGAC | AAAAGCCTTA | 2460 |
| TCTGCTGGTA | CAACGGAAAT | TGTAAATGCC | CACGATAAAG | TCCGTTTTGC | TAATGGTTTA | 2520 |
| AATACCAAAG | TGAGCGCGGC | AACGGTGGAA | AGCACCGATG | CAAACGGCGA | TAAAGTGACC | 2580 |
| ACAACCTTTG | TGAAAACCGA | TGTGGAATTG | CCTTTAACGC | AAATCTACAA | TACCGATGCA | 2640 |
| AACGGTAAGA | AAATCACTAA | AGTTGTCAAA | GATGGGCAAA | CTAAATGGTA | TGAACTGAAT | 2700 |
| GCTGACGGTA | CGGCTGATAT | GACCAAAGAA | GTTACCCTCG | GTAACGTGGA | TTCAGACGGC | 2760 |
| AAGAAAGTTG | TGAAAGACAA | CGATGGCAAG | TGGTATCACG | CCAAAGCTGA | CGGTACTGCG | 2820 |
| GATAAAACCA | AAGGCGAAGT | GAGCAATGAT | AAAGTTTCTA | CCGATGAAAA | ACACGTTGTC | 2880 |
| AGCCTTGATC | CAAATGATCA | ATCAAAAGGT | AAAGGTGTCG | TGATTGACAA | TGTGGCTAAT | 2940 |
| GGCGATATTT | CTGCCACTTC | CACCGATGCG | ATTAACGGAA | GTCAGTTGTA | TGCTGTGGCA | 3000 |
| AAAGGGGTAA | CAAACCTTGC | TGGACAAGTG | AATAATCTTG | AGGGCAAAGT | GAATAAAGTG | 3060 |
| GGCAAACGTG | CAGATGCAGG | TACAGCAAGT | GCATTAGCGG | CTTCACAGTT | ACCACAAGCC | 3120 |
| ACTATGCCAG | GTAAATCAAT | GGTTGCTATT | GCGGGAAGTA | GTTATCAAGG | TCAAAATGGT | 3180 |
| TTAGCTATCG | GGGTATCAAG | AATTTCCGAT | AATGGCAAAG | TGATTATTCG | CTTGTCAGGC | 3240 |
| ACAACCAATA | GTCAAGGTAA | AACAGGCGTT | GCAGCAGGTG | TTGGTTACCA | GTGG | 3294 |

FIG._1B

```
Met Asn Lys Ile Phe Asn Val Ile Trp Asn Val Val Thr Gln Thr Trp
1               5               10                  15
Val Val Val Ser Glu Leu Thr Arg Thr His Thr Lys Cys Ala Ser Ala
            20              25              30
Thr Val Ala Val Ala Val Leu Ala Thr Leu Leu Ser Ala Thr Val Glu
        35              40              45
Ala Asn Asn Asn Thr Pro Val Thr Asn Lys Leu Lys Ala Tyr Gly Asp
50              55              60
Ala Asn Phe Asn Phe Thr Asn Asn Ser Ile Ala Asp Ala Glu Lys Gln
65              70              75              80
Val Gln Glu Ala Tyr Lys Gly Leu Leu Asn Leu Asn Glu Lys Asn Ala
            85              90              95
Ser Asp Lys Leu Leu Val Glu Asp Asn Thr Ala Ala Thr Val Gly Asn
            100             105             110
Leu Arg Lys Leu Gly Trp Val Leu Ser Ser Lys Asn Gly Thr Arg Asn
        115             120             125
Glu Lys Ser Gln Gln Val Lys His Ala Asp Glu Val Leu Phe Glu Gly
    130             135             140
Lys Gly Gly Val Gln Val Thr Ser Thr Ser Glu Asn Gly Lys His Thr
145             150             155             160
Ile Thr Phe Ala Leu Ala Lys Asp Leu Gly Val Lys Thr Ala Thr Val
            165             170             175
Ser Asp Thr Leu Thr Ile Gly Gly Ala Ala Ala Gly Ala Thr Thr
            180             185             190
Thr Pro Lys Val Asn Val Thr Ser Thr Thr Asp Gly Leu Lys Phe Ala
        195             200             205
Lys Asp Ala Ala Gly Ala Asn Gly Asp Thr Thr Val His Leu Asn Gly
    210             215             220
Ile Gly Ser Thr Leu Thr Asp Thr Leu Val Gly Ser Pro Ala Thr His
225             230             235             240
Ile Asp Gly Gly Asp Gln Ser Thr His Tyr Thr Arg Ala Ala Ser Ile
            245             250             255
Lys Asp Val Leu Asn Ala Gly Trp Asn Ile Lys Gly Val Lys Ala Gly
            260             265             270
Ser Thr Thr Gly Gln Ser Glu Asn Val Asp Phe Val His Thr Tyr Asp
        275             280             285
```

FIG._2A

```
Thr Val Glu Phe Leu Ser Ala Asp Thr Glu Thr Thr Val Thr Val
    290                 295                 300
Asp Ser Lys Glu Asn Gly Lys Arg Thr Glu Val Lys Ile Gly Ala Lys
305                 310                 315                 320
Thr Ser Val Ile Lys Glu Lys Asp Gly Lys Leu Phe Thr Gly Lys Ala
                325                 330                 335
Asn Lys Glu Thr Asn Lys Val Asp Gly Ala Asn Ala Thr Glu Asp Ala
            340                 345                 350
Asp Glu Gly Lys Gly Leu Val Thr Ala Lys Asp Val Ile Asp Ala Val
            355                 360                 365
Asn Lys Thr Gly Trp Arg Ile Lys Thr Thr Asp Ala Asn Gly Gln Asn
    370                 375                 380
Gly Asp Phe Ala Thr Val Ala Ser Gly Thr Asn Val Thr Phe Ala Ser
385                 390                 395                 400
Gly Asn Gly Thr Thr Ala Thr Val Thr Asn Gly Thr Asp Gly Ile Thr
                405                 410                 415
Val Lys Tyr Asp Ala Lys Val Gly Asp Gly Leu Lys Leu Asp Gly Asp
            420                 425                 430
Lys Ile Ala Ala Asp Thr Thr Ala Leu Thr Val Asn Asp Gly Lys Asn
        435                 440                 445
Ala Asn Asn Pro Lys Gly Lys Val Ala Asp Val Ala Ser Thr Asp Glu
    450                 455                 460
Lys Lys Leu Val Thr Ala Lys Gly Leu Val Thr Ala Leu Asn Ser Leu
465                 470                 475                 480
Ser Trp Thr Thr Thr Ala Ala Glu Ala Asp Gly Gly Thr Leu Asp Gly
            485                 490                 495
Asn Ala Ser Glu Gln Glu Val Lys Ala Gly Asp Lys Val Thr Phe Lys
                500                 505                 510
Ala Gly Lys Asn Leu Lys Val Lys Gln Glu Gly Ala Asn Phe Thr Tyr
        515                 520                 525
Ser Leu Gln Asp Ala Leu Thr Gly Leu Thr Ser Ile Thr Leu Gly Thr
    530                 535                 540
Gly Asn Asn Gly Ala Lys Thr Glu Ile Asn Lys Asp Gly Leu Thr Ile
545                 550                 555                 560
Thr Pro Ala Asn Gly Ala Gly Ala Asn Asn Ala Asn Thr Ile Ser Val
                565                 570                 575
Thr Lys Asp Gly Ile Ser Ala Gly Gly Gln Ser Val Lys Asn Val Val
            580                 585                 590
```

*FIG._2B*

```
Ser Gly Leu Lys Lys Phe Gly Asp Ala Asn Phe Asp Pro Leu Thr Ser
        595                 600                 605

Ser Ala Asp Asn Leu Thr Lys Gln Asn Asp Ala Tyr Lys Gly Leu
    610                 615                 620

Thr Asn Leu Asp Glu Lys Gly Thr Asp Lys Gln Thr Pro Val Val Ala
625                 630                 635                 640

Asp Asn Thr Ala Ala Thr Val Gly Asp Leu Arg Gly Leu Gly Trp Val
            645                 650                 655

Ile Ser Ala Asp Lys Thr Thr Gly Gly Ser Thr Glu Tyr His Asp Gln
            660                 665                 670

Val Arg Asn Ala Asn Glu Val Lys Phe Lys Ser Gly Asn Gly Ile Asn
                675                 680                 685

Val Ser Gly Lys Thr Val Asn Gly Arg Arg Glu Ile Thr Phe Glu Leu
    690                 695                 700

Ala Lys Gly Glu Val Val Lys Ser Asn Glu Phe Thr Val Lys Glu Thr
705                 710                 715                 720

Asn Gly Lys Glu Thr Ser Leu Val Lys Val Gly Asp Lys Tyr Tyr Ser
                725                 730                 735

Lys Glu Asp Ile Asp Leu Thr Thr Gly Gln Pro Lys Leu Lys Asp Gly
            740                 745                 750

Asn Thr Val Ala Ala Lys Tyr Gln Asp Lys Gly Gly Lys Val Val Ser
    755                 760                 765

Val Thr Asp Asn Thr Glu Ala Thr Ile Thr Asn Lys Gly Ser Gly Tyr
    770                 775                 780

Val Thr Gly Asn Gln Val Ala Asp Ala Ile Ala Lys Ser Gly Phe Glu
785                 790                 795                 800

Leu Gly Leu Ala Asp Glu Ala Asp Ala Lys Arg Ala Phe Asp Asp Lys
            805                 810                 815

Thr Lys Ala Leu Ser Ala Gly Thr Thr Glu Ile Val Asn Ala His Asp
            820                 825                 830

Lys Val Arg Phe Ala Asn Gly Leu Asn Thr Lys Val Ser Ala Ala Thr
        835                 840                 845

Val Glu Ser Thr Asp Ala Asn Gly Asp Lys Val Thr Thr Thr Phe Val
    850                 855                 860

Lys Thr Asp Val Glu Leu Pro Leu Thr Gln Ile Tyr Asn Thr Asp Ala
865                 870                 875                 880

Asn Gly Lys Lys Ile Thr Lys Val Val Lys Asp Gly Gln Thr Lys Trp
            885                 890                 895
```

FIG._2C

```
Tyr Glu Leu Asn Ala Asp Gly Thr Ala Asp Met Thr Lys Glu Val Thr
            900                 905                 910
Leu Gly Asn Val Asp Ser Asp Gly Lys Lys Val Val Lys Asp Asn Asp
            915                 920                 925
Gly Lys Trp Tyr His Ala Lys Ala Asp Gly Thr Ala Asp Lys Thr Lys
    930                 935                 940
Gly Glu Val Ser Asn Asp Lys Val Ser Thr Asp Glu Lys His Val Val
945                 950                 955                 960
Ser Leu Asp Pro Asn Asp Gln Ser Lys Gly Lys Gly Val Val Ile Asp
                965                 970                 975
Asn Val Ala Asn Gly Asp Ile Ser Ala Thr Ser Thr Asp Ala Ile Asn
            980                 985                 990
Gly Ser Gln Leu Tyr Ala Val Ala Lys Gly Val Thr Asn Leu Ala Gly
        995                 1000                1005
Gln Val Asn Asn Leu Glu Gly Lys Val Asn Lys Val Gly Lys Arg Ala
    1010                1015                1020
Asp Ala Gly Thr Ala Ser Ala Leu Ala Ala Ser Gln Leu Pro Gln Ala
1025                1030                1035                1040
Thr Met Pro Gly Lys Ser Met Val Ala Ile Ala Gly Ser Ser Tyr Gln
                1045                1050                1055
Gly Gln Asn Gly Leu Ala Ile Gly Val Ser Arg Ile Ser Asp Asn Gly
                1060                1065                1070
Lys Val Ile Ile Arg Leu Ser Gly Thr Thr Asn Ser Gln Gly Lys Thr
            1075                1080                1085
Gly Val Ala Ala Gly Val Gly Tyr Gln Trp
1090                1095
```

FIG._2D

```
ATGAACAAAA TTTTTAACGT TATTTGGAAT GTTATGACTC AAACTTGGGT TGTCGTATCT    60
GAACTCACTC GCACCCACAC CAAACGCCTC CGCAACCGTG GAGACCCCGT ATTGGCGACA   120
CTGTTGTTTG CAACGGTTCA GGCGAATGCT ACCGATGAAG ATGAAGAGTT AGACCCCGTA   180
GTACGCACTG CTCCCGTGTT GAGCTTCCAT TCCGATAAAG AAGGCACGGG AGAAAAGAA    240
GTTACAGAAA ATTCAAATTG GGAATATAT TTCGACAATA AGGAGTACT AAAAGCCGGA    300
GCAATCACCC TCAAAGCCGG CGACAACCTG AAAATNAAAC AAAaNaCCGA TGAAAGNACC   360
AATGCCAGTA GCTTCACCTA CTCGCTGAAA AAAGACCTCA CAGATCTGAC CAGTGTTGCA   420
ACTGAAAAAT TATCGTTTGG CGCAAACGGC GATAAAGTTG ATATTACCAG TGATGCAAAT   480
GGCTTGAAAT TGGCGAAAAC AGGTAACGGA AATGTTCATT TGAATGGTTT GGATTCAACT   540
TTGCCTGATG CGGTAACGAA TACAGGTGTG TTAAGTTCAT CAAGTTTTAC ACCTAATGAT   600
GTTGAAAAAA CAAGAGCTGC AACTGTTAAA GATGTTTTAA ATGCAGGTTG GAACATTAAA   660
GGTGCTAAAA CTGCTGGAGG TAATGTTGAG AGTGTTGATT TAGTGTCCGC TTATAATAAT   720
GTTGAATTTA TTACAGGCGA TAAAAACACG CTTGATGTTG TATTAACAGC TAAAGAAAAC   780
NGTAAAACAA CCGAAGTGAA ATTCACACCG AAAACCTCTG TTATCAAAGA AAAAGACGGT   840
AAGTTATTTA CTGGAAAAGA GAATAACGAC ACAAATAAAG TTACAAGTAA CACGGCGACT   900
GATAATACAG ATGAGGGTAA TGGCTTAGTC ACTGCAAAAG CTGTGATTGA TGCTGTGAAC   960
AAGGCTGGTT GGAGAGTTAA ACAACTACT GCTAATGGTC AAAATGGCGA CTTCGCAACT  1020
GTTGCGTCAG GCACAAATGT AACCTTTGAA AGTGGCGATG GTACAACAGC GTCAGTAACT  1080
AAAGATACTA ACGGCAATGG CATCACTGTT AAGTACGACG CGAAAGTTGG CGACGGCTTG  1140
AAATTTGATA GCGATAAAAA AATCGTTGCA GATACGACCG CACTTACTGT GACAGGTGGT  1200
AAGGTAGCTG AAATTGCTAA AGAAGATGAC AAGAAAAAAC TTGTTAATGC AGGCGATTTG  1260
GTAACAGCTT TAGGTAATCT AAGTTGGAAA GCAAAAGCTG AGGCTGATAC TGATGGTGCG  1320
CTTGAGGGGA TTTCAAAAGA CCAAGAAGTC AAAGCAGGCG AAACGGTAAC CTTTAAAGCG  1380
```

FIG._3A

```
GGCAAGAACT TAAAAGTGAA ACAGGATGGT GCGAACTTTA CTTATTCACT GCAAGATGCT    1440
TTAACGGGTT TAACGAGCAT TACTTTAGGT GGTACAACTA ATGGCGGAAA TGATGCGAAA    1500
ACCGTCATCA ACAAAGACGG TTTAACCATC ACGCCAGCAG GTAATGGCGG TACGACAGGT    1560
ACAAACACCA TCAGCGTAAC CAAAGATGGC ATTAAAGCAG GTAATAAAGC TATTACTAAT    1620
GTTGCGAGTG GgTTAAGAGC TTATGACGAT GCGAATTTTg ATGTTTTAAA TAACTCTGCA    1680
ACTGATTTAA ATAGACACGT TGAAGATGCT TATAAAGGTT TATTAAATCT AAATGAAAAA    1740
AATGCAAATA ACAACCGTT GGTGACTGAC AGCACGGCGG CGACTGTAGG CGATTTACGT     1800
AAATTGGGTT GGGTAGTATC AACCAAAAAC GGTACGAAAG AAGAAAGCAA TCAAGTTAAA    1860
CAAGCTGATG AAGTCCTCTT TACCGGAGCC GGTGCTGCTA CGGTTACTTC CAAATCTGAA    1920
ACGGTAAAC ATACGATTAC CGTTAGTGTG GCTGAAACTA AGCGGATTG CGGTCTTGAA      1980
AAAGATGGCG ATACTATTAA GCTCAAAGTG GATAATCAAA ACACTGATAA TGTTTTAACT    2040
GTTGGTAATA ATGGTACTGC TGTCACTAAA GGTGGCTTTG AAACTGTTAA AACTGGAGCG    2100
ACTGATGCAG ATCGCGGTAA AGTAACTGTA AAAGATGCTA CTGCTAATGA CGCTGATAAG    2160
AAAGTCGCAA CTGTAAAAGA TGTTGCAACC GCAATTAATA GTGCGGCGAC TTTTGTGAAA    2220
ACAGAGAATT TAACTACCTC TATTGATGAA GATAATCCTA CAGATAACGG CAAAGATGAC    2280
GCACTTAAAG CGGGCGATAC CTTAACCTTT AAAGCAGGTA AAAACCTGAA AGTTAAACGT    2340
GATGGAAAAA ATATTACTTT TGACTTGGCN AAAAACCTTG AGGTGAAAAC TGCGAAAGTG    2400
AGTGATACTT TAACGATTGG CGGGAATACA CCTACAGGTG GCACTACTGC GACGCCAAAA    2460
GTGAATATTA CTAGCACGGC TGATGGTTTG AATTTTGCAA AGAAACAGC CGATGCCTCG     2520
GGTTCTAAGA ATGTTTATTT GAAAGGTATT GCGACAACTT TAACTGAGCC AAGCGCGGGA    2580
GCGAAGTCTT CACACGTTGA TTTAAATGTG GATGCGACGA AAAAATCCAA TGCAGCAAGT    2640
ATTGAAGATG TATTGCGCGC AGGTTGGAAT ATTCAAGGTA ATGGTAATAA TGTTGATTAT    2700
GTAGCGACGT ATGACACAGT AAACTTTACC GATGACAGCA CAGGTACAAC AACGGTAACC    2760
```

FIG._3B

```
GTAACCCAAA AAGCAGATGG CAAAGGTGCT GACGTTAAAA TCGGTGCGAA AACTTCTGTT    2820
ATCAAAGACC ACAACGGCAA ACTGTTTACA GGCAAAGACC TGAAAGATGC GAATAATGGT    2880
GCAACCGTTA GTGAAGATGA TGGCAAAGAC ACCGGCACAG CTTAGTTAC TGCAAAAACT     2940
GTGATTGATG CAGTAAATAA AAGCGGTTGG AGGGTAACCG GTGAGGGCGC GACTGCCGAA    3000
ACCGGTGCAA CCGCCGTGAA TGCGGGTAAC GCTGAAACCG TTACATCAGG CACGAGCGTG    3060
AACTTCAAAA ACGGCAATGC GACCACAGCG ACCGTAAGCA AGATAATGG CAACATCAAT     3120
GTCAAATACG ATGTAAATGT TGGTGACGGC TTGAAGATTG GCGATGACAA AAAAATCGTT    3180
GCAGACACGA CCACACTTAC TGTAACAGGT GGTAAGGTGT CTGTTCCTGC TGGTGCTAAT    3240
AGTGTTAATA ACAATAAGAA ACTTGTTAAT GCAGAGGGTT TAGCGACTGC TTTAAACAAC    3300
CTAAGCTGGA CgGCAAAAGC CGATAAATAT GCAGATGGCG AGTCAGAGGG CGAAACCGAC    3360
CAAGAAGTCA AGCAGGCGA CAAAGTAACC TTTAAAGCAG GCAAGAACTT AAAAGTGAAA     3420
CAGTCTGAAA AAGACTTTAC TTATTCACTG CAAGACACTT TAACAGGCTT AACGAGCATT    3480
ACTTTAGGTG GTACAGCTAA TGGCAGAAAT GATACGGGAA CCGTCATCAA CAAAGACGGC    3540
TTAACCATCA CGCTGGCAAA TGGTGCTGCG GCAGGCACAG ATGCGTCTAA CGGAAACACC    3600
ATCAGTGTAA CCAAAGACGG CATTAGTGCG GGTAATAAAG AAATTACCAA TGTTAAGAGT    3660
GCTTTAAAAA CCTATAAAGA TACTCAAAAC ACTGCAGATG AAACACAAGA TAAAGAGTTC    3720
CACGCCGCCG TTAAAAACGC AAATGAAGTT GAGTTCGTGG GTAAAAACGG TGCAACCGTG    3780
TCTGCAAAAA CTGATAACAA CGGAAAACAT ACTGTAACGA TTGATGTTGC AGAAGCCAAA    3840
GTTGGTGATG GTCTTGAAAA AGATACTGAC GGCAAGATTA AACTCAAAGT AGATAATACA    3900
GATGGGAATA ATCTATTAAC CGTTGATGCA ACAAAAGGTG CATCCGTTGC CAAGGGCGAG    3960
TTTAATGCCG TAACAACAGA TGCAACTACA GCCCAAGGcA CAAATGCCAA TGAGCGCgGT    4020
AAAGTGGTTG TCAAGGGTTC AAATGGTGCA ACTGCTACCG AAACTGACAA GAAAAAagTG    4080
GCAACTGTTG GCGACGTTGC TAAAGCgATT AACGACGCAG CAACTTTCGT GAAAGTGGAA    4140
```

FIG._3C

```
AATGACGACA GTGCTACGAT TGATGATAGC CCAACAGATG ATGGCGCAAA TGATGCTCTC    4200

AAAGCANgCG ACACCTTGAC CTTAAAAGCG GGTAAAAACT TAAAAGTTAA ACGTGATGGT    4260

AAAAATATTA CTTTTGCCCT TGCGAACGAC CTTAGTGTAA AAAGCGCAAC CGTTAGCGAT    4320

AAATTATCGC TTGGTACAAA CGGCAATAAA GTCAATATCA AAGCGACAC CAAAGGCTTG     4380

AACTTCGCTA AAGATAGTAA GACAGGCGAT GATGCTAATA TTCACTTAAA TGGCATTGCT    4440

TCAACTTTAA CTGATACATT GTTAAATAGT GGTGCGACAA CCAATTTAGG TGGTAATGGT    4500

ATTACTGATA ACGAGAAAAA ANNCGCggCG AGcGTTAAAG ATGTCTTGAA TGCGGGTTGG    4560

AATGTTCGTG GTGTTAAACC GGCATCTGCA AATAATCAAG TGGAGAATAT CGACTTTGTA    4620

GCAACCTACG ACACAGTGGA CTTTGTTAGT GGAGATAAAG ACACCACGAG TGTAACTGTT    4680

GAAAGTAAAG ATAATGGCAA GAGAACCGAA GTTAAAATCG GTGCGAAGAC TTCTGTTATC    4740

AAAGACCACA ACGGCAAACT GTTTACAGGC AAAGAGCTGA AGGATGCTAA CAATAATGGC    4800

GTAACTGTTA CCGAAACCGA CGGCAAAGAC GAGGGTAATG GTTTAGTGAC TGCAAAAGCT    4860

GTGATTGATg CCGTGAATAA GGCTGGTTGG AGAGTTAAAA CAACAGGTGC TAATGGTCAG    4920

AATGATGACT TCGCAACTGT TGCGTCAGGC ACAAATGTAA CCTTTGCTGA TGGTAATGGC    4980

ACAACTGCCG AAGTAACTAA AGCAAACGAC GGTAGTATTA CTGTTAAATA CAATGTTAAA    5040

GTGGCTGATG GCTTAAAACT AGACGGCGAT AAAATCGTTG CAGACACGAC CGTACTTACT    5100

GTGGCAGATG GTAAAGTTAC AGCTCCGAAT AATGGCNATG GTAAGAAATT TNTTGATGCA    5160

AGTGGTTTAG CggGATgcTT AAATAAATTA AGcTNGACgG CAACTGCTGG TAAAGAAGGC    5220

ACTGGTGAAG TTGATCCTGC AAATTCAGCA GGGCAAGAAG TCAAAGCGGG CGACAAAGTA    5280

ACCTTTAAAG CCGGCGACAA CCTGAAAATC AAACAAAGCG NCAAAGACTT TACCTACTCG    5340

CTGAAAAAAG AGCTGAAAGA CCTGACCAGC GTAGAGTTCA AAGACGCAAA CGGCGGTACA    5400

GGCAGTGAAA GCACCAAGAT TACCAAAGAC GGCTTGACCA TTACGCCGGC AAACGGTGCG    5460

GGTGCGGCAG GTGCAAACAC TGCAAACACC ATTAGCGTAA CCAAAGATGG CATTAGCGCG    5520

GGTAATAAAg caGTTACAAA CGTTGTGAGC GGACTGAAGA AATTTGGTGA TGGTCATACG    5580

TTGGCAAATG GCACTGTTGC TGATTTTGAA AAGCATTATG ACAATGCCTA TAANGACTTG    5640

ACCAATTTGG ATGAANANNC NCgGATAATA ATCCGACTGT TGCCGACAAT ACCGCTGCAA    5700

CCGTGGGCGA TTTNNNNGGC TTGGGCTGGG TCATTTCT                            5738
```

FIG._3D

Met Asn Lys Ile Phe Asn Val Ile Trp Asn Val Met Thr Gln Thr Trp
1             5                   10                  15

Val Val Val Ser Glu Leu Thr Arg Thr His Thr Lys Arg Leu Arg Asn
            20                  25                  30

Arg Gly Asp Pro Val Leu Ala Thr Leu Leu Phe Ala Thr Val Gln Ala
        35                  40                  45

Asn Ala Thr Asp Glu Asp Glu Glu Leu Asp Pro Val Val Arg Thr Ala
50                      55                  60

Pro Val Leu Ser Phe His Ser Asp Lys Glu Gly Thr Gly Glu Lys Glu
65                  70                  75                  80

Val Thr Glu Asn Ser Asn Trp Gly Ile Tyr Phe Asp Asn Lys Gly Val
                85                  90                  95

Leu Lys Ala Gly Ala Ile Thr Leu Lys Ala Gly Asp Asn Leu Lys Xaa
            100                 105                 110

Lys Gln Xaa Thr Asp Glu Xaa Thr Asn Ala Ser Ser Phe Thr Tyr Ser
        115                 120                 125

Leu Lys Lys Asp Leu Thr Asp Leu Thr Ser Val Ala Thr Glu Lys Leu
130                 135                 140

Ser Phe Gly Ala Asn Gly Asp Lys Val Asp Ile Thr Ser Asp Ala Asn
145                 150                 155                 160

Gly Leu Lys Leu Ala Lys Thr Gly Asn Gly Asn Val His Leu Asn Gly
            165                 170                 175

Leu Asp Ser Thr Leu Pro Asp Ala Val Thr Asn Thr Gly Val Leu Ser
        180                 185                 190

Ser Ser Ser Phe Thr Pro Asn Asp Val Glu Lys Thr Arg Ala Ala Thr
        195                 200                 205

Val Lys Asp Val Leu Asn Ala Gly Trp Asn Ile Lys Gly Ala Lys Thr
210                 215                 220

Ala Gly Gly Asn Val Glu Ser Val Asp Leu Val Ser Ala Tyr Asn Asn
225                 230                 235                 240

Val Glu Phe Ile Thr Gly Asp Lys Asn Thr Leu Asp Val Val Leu Thr
            245                 250                 255

Ala Lys Glu Asn Xaa Lys Thr Thr Glu Val Lys Phe Thr Pro Lys Thr
        260                 265                 270

Ser Val Ile Lys Glu Lys Asp Gly Lys Leu Phe Thr Gly Lys Glu Asn
        275                 280                 285

Asn Asp Thr Asn Lys Val Thr Ser Asn Thr Ala Thr Asp Asn Thr Asp
290                 295                 300

FIG._4A

```
Glu Gly Asn Gly Leu Val Thr Ala Lys Ala Val Ile Asp Ala Val Asn
305                 310                 315                 320

Lys Ala Gly Trp Arg Val Lys Thr Thr Thr Ala Asn Gly Gln Asn Gly
                325                 330                 335

Asp Phe Ala Thr Val Ala Ser Gly Thr Asn Val Thr Phe Glu Ser Gly
                340                 345                 350

Asp Gly Thr Thr Ala Ser Val Thr Lys Asp Thr Asn Gly Asn Gly Ile
        355                 360                 365

Thr Val Lys Tyr Asp Ala Lys Val Gly Asp Gly Leu Lys Phe Asp Ser
    370                 375                 380

Asp Lys Lys Ile Val Ala Asp Thr Thr Ala Leu Thr Val Thr Gly Gly
385                 390                 395                 400

Lys Val Ala Glu Ile Ala Lys Glu Asp Asp Lys Lys Lys Leu Val Asn
                405                 410                 415

Ala Gly Asp Leu Val Thr Ala Leu Gly Asn Leu Ser Trp Lys Ala Lys
            420                 425                 430

Ala Glu Ala Asp Thr Asp Gly Ala Leu Glu Gly Ile Ser Lys Asp Gln
        435                 440                 445

Glu Val Lys Ala Gly Glu Thr Val Thr Phe Lys Ala Gly Lys Asn Leu
    450                 455                 460

Lys Val Lys Gln Asp Gly Ala Asn Phe Thr Tyr Ser Leu Gln Asp Ala
465                 470                 475                 480

Leu Thr Gly Leu Thr Ser Ile Thr Leu Gly Gly Thr Thr Asn Gly Gly
            485                 490                 495

Asn Asp Ala Lys Thr Val Ile Asn Lys Asp Gly Leu Thr Ile Thr Pro
                500                 505                 510

Ala Gly Asn Gly Gly Thr Thr Gly Thr Asn Thr Ile Ser Val Thr Lys
            515                 520                 525

Asp Gly Ile Lys Ala Gly Asn Lys Ala Ile Thr Asn Val Ala Ser Gly
        530                 535                 540

Leu Arg Ala Tyr Asp Asp Ala Asn Phe Asp Val Leu Asn Asn Ser Ala
545                 550                 555                 560

Thr Asp Leu Asn Arg His Val Glu Asp Ala Tyr Lys Gly Leu Leu Asn
                565                 570                 575

Leu Asn Glu Lys Asn Ala Asn Lys Gln Pro Leu Val Thr Asp Ser Thr
            580                 585                 590

Ala Ala Thr Val Gly Asp Leu Arg Lys Leu Gly Trp Val Val Ser Thr
        595                 600                 605
```

FIG._4B

```
Lys Asn Gly Thr Lys Glu Glu Ser Asn Gln Val Lys Gln Ala Asp Glu
610             615                 620

Val Leu Phe Thr Gly Ala Gly Ala Ala Thr Val Thr Ser Lys Ser Glu
625             630                 635                 640

Asn Gly Lys His Thr Ile Thr Val Ser Val Ala Glu Thr Lys Ala Asp
                645                 650                 655

Cys Gly Leu Glu Lys Asp Gly Asp Thr Ile Lys Leu Lys Val Asp Asn
            660                 665                 670

Gln Asn Thr Asp Asn Val Leu Thr Val Gly Asn Asn Gly Thr Ala Val
            675             680                 685

Thr Lys Gly Gly Phe Glu Thr Val Lys Thr Gly Ala Thr Asp Ala Asp
    690             695                 700

Arg Gly Lys Val Thr Val Lys Asp Ala Thr Ala Asn Asp Ala Asp Lys
705             710                 715                 720

Lys Val Ala Thr Val Lys Asp Val Ala Thr Ala Ile Asn Ser Ala Ala
                725                 730                 735

Thr Phe Val Lys Thr Glu Asn Leu Thr Thr Ser Ile Asp Glu Asp Asn
            740                 745                 750

Pro Thr Asp Asn Gly Lys Asp Asp Ala Leu Lys Ala Gly Asp Thr Leu
        755                 760                 765

Thr Phe Lys Ala Gly Lys Asn Leu Lys Val Lys Arg Asp Gly Lys Asn
770                 775                 780

Ile Thr Phe Asp Leu Ala Lys Asn Leu Glu Val Lys Thr Ala Lys Val
785             790                 795                 800

Ser Asp Thr Leu Thr Ile Gly Gly Asn Thr Pro Thr Gly Gly Thr Thr
            805                 810                 815

Ala Thr Pro Lys Val Asn Ile Thr Ser Thr Ala Asp Gly Leu Asn Phe
        820                 825                 830

Ala Lys Glu Thr Ala Asp Ala Ser Gly Ser Lys Asn Val Tyr Leu Lys
        835                 840                 845

Gly Ile Ala Thr Thr Leu Thr Glu Pro Ser Ala Gly Ala Lys Ser Ser
    850             855                 860

His Val Asp Leu Asn Val Asp Ala Thr Lys Lys Ser Asn Ala Ala Ser
865             870                 875                 880

Ile Glu Asp Val Leu Arg Ala Gly Trp Asn Ile Gln Gly Asn Gly Asn
            885                 890                 895

Asn Val Asp Tyr Val Ala Thr Tyr Asp Thr Val Asn Phe Thr Asp Asp
            900                 905                 910
```

FIG._4C

```
Ser Thr Gly Thr Thr Thr Val Thr Val Thr Gln Lys Ala Asp Gly Lys
    915                 920                 925

Gly Ala Asp Val Lys Ile Gly Ala Lys Thr Ser Val Ile Lys Asp His
    930                 935                 940

Asn Gly Lys Leu Phe Thr Gly Lys Asp Leu Lys Asp Ala Asn Asn Gly
945                 950                 955                 960

Ala Thr Val Ser Glu Asp Asp Gly Lys Asp Thr Gly Thr Gly Leu Val
                965                 970                 975

Thr Ala Lys Thr Val Ile Asp Ala Val Asn Lys Ser Gly Trp Arg Val
            980                 985                 990

Thr Gly Glu Gly Ala Thr Ala Glu Thr Gly Ala Thr Ala Val Asn Ala
        995                 1000                1005

Gly Asn Ala Glu Thr Val Thr Ser Gly Thr Ser Val Asn Phe Lys Asn
    1010                1015                1020

Gly Asn Ala Thr Thr Ala Thr Val Ser Lys Asp Asn Gly Asn Ile Asn
1025                1030                1035                1040

Val Lys Tyr Asp Val Asn Val Gly Asp Gly Leu Lys Ile Gly Asp Asp
                1045                1050                1055

Lys Lys Ile Val Ala Asp Thr Thr Leu Thr Val Thr Gly Gly Lys
                1060                1065                1070

Val Ser Val Pro Ala Gly Ala Asn Ser Val Asn Asn Lys Lys Leu
    1075                1080                1085

Val Asn Ala Glu Gly Leu Ala Thr Ala Leu Asn Asn Leu Ser Trp Thr
    1090                1095                1100

Ala Lys Ala Asp Lys Tyr Ala Asp Gly Glu Ser Glu Gly Glu Thr Asp
1105                1110                1115                1120

Gln Glu Val Lys Ala Gly Asp Lys Val Thr Phe Lys Ala Gly Lys Asn
                1125                1130                1135

Leu Lys Val Lys Gln Ser Glu Lys Asp Phe Thr Tyr Ser Leu Gln Asp
                1140                1145                1150

Thr Leu Thr Gly Leu Thr Ser Ile Thr Leu Gly Gly Thr Ala Asn Gly
            1155                1160                1165

Arg Asn Asp Thr Gly Thr Val Ile Asn Lys Asp Gly Leu Thr Ile Thr
        1170                1175                1180

Leu Ala Asn Gly Ala Ala Ala Gly Thr Asp Ala Ser Asn Gly Asn Thr
1185                1190                1195                1200

Ile Ser Val Thr Lys Asp Gly Ile Ser Ala Gly Asn Lys Glu Ile Thr
                1205                1210                1215
```

FIG._4D

```
Asn Val Lys Ser Ala Leu Lys Thr Tyr Lys Asp Thr Gln Asn Thr Ala
            1220                1225                1230

Asp Glu Thr Gln Asp Lys Glu Phe His Ala Ala Val Lys Asn Ala Asn
            1235                1240                1245

Glu Val Glu Phe Val Gly Lys Asn Gly Ala Thr Val Ser Ala Lys Thr
            1250                1255                1260

Asp Asn Asn Gly Lys His Thr Val Thr Ile Asp Val Ala Glu Ala Lys
1265                1270                1275                1280

Val Gly Asp Gly Leu Glu Lys Asp Thr Asp Gly Lys Ile Lys Leu Lys
                1285                1290                1295

Val Asp Asn Thr Asp Gly Asn Asn Leu Leu Thr Val Asp Ala Thr Lys
            1300                1305                1310

Gly Ala Ser Val Ala Lys Gly Glu Phe Asn Ala Val Thr Thr Asp Ala
            1315                1320                1325

Thr Thr Ala Gln Gly Thr Asn Ala Asn Glu Arg Gly Lys Val Val Val
            1330                1335                1340

Lys Gly Ser Asn Gly Ala Thr Ala Thr Glu Thr Asp Lys Lys Lys Val
1345                1350                1355                1360

Ala Thr Val Gly Asp Val Ala Lys Ala Ile Asn Asp Ala Ala Thr Phe
            1365                1370                1375

Val Lys Val Glu Asn Asp Asp Ser Ala Thr Ile Asp Asp Ser Pro Thr
            1380                1385                1390

Asp Asp Gly Ala Asn Asp Ala Leu Lys Ala Xaa Asp Thr Leu Thr Leu
            1395                1400                1405

Lys Ala Gly Lys Asn Leu Lys Val Lys Arg Asp Gly Lys Asn Ile Thr
    1410                1415                1420

Phe Ala Leu Ala Asn Asp Leu Ser Val Lys Ser Ala Thr Val Ser Asp
1425                1430                1435                1440

Lys Leu Ser Leu Gly Thr Asn Gly Asn Lys Val Asn Ile Thr Ser Asp
            1445                1450                1455

Thr Lys Gly Leu Asn Phe Ala Lys Asp Ser Lys Thr Gly Asp Asp Ala
            1460                1465                1470

Asn Ile His Leu Asn Gly Ile Ala Ser Thr Leu Thr Asp Thr Leu Leu
            1475                1480                1485

Asn Ser Gly Ala Thr Thr Asn Leu Gly Gly Asn Gly Ile Thr Asp Asn
            1490                1495                1500

Glu Lys Lys Xaa Ala Ala Ser Val Lys Asp Val Leu Asn Ala Gly Trp
1505                1510                1515                1520
```

FIG._4E

```
Asn Val Arg Gly Val Lys Pro Ala Ser Ala Asn Asn Gln Val Glu Asn
                1525                1530                1535

Ile Asp Phe Val Ala Thr Tyr Asp Thr Val Asp Phe Val Ser Gly Asp
            1540                1545                1550

Lys Asp Thr Thr Ser Val Thr Val Glu Ser Lys Asp Asn Gly Lys Arg
            1555                1560                1565

Thr Glu Val Lys Ile Gly Ala Lys Thr Ser Val Ile Lys Asp His Asn
        1570            1575                1580

Gly Lys Leu Phe Thr Gly Lys Glu Leu Lys Asp Ala Asn Asn Asn Gly
1585                1590                1595                1600

Val Thr Val Thr Glu Thr Asp Gly Lys Asp Glu Gly Asn Gly Leu Val
                1605                1610                1615

Thr Ala Lys Ala Val Ile Asp Ala Val Asn Lys Ala Gly Trp Arg Val
                1620                1625                1630

Lys Thr Thr Gly Ala Asn Gly Gln Asn Asp Asp Phe Ala Thr Val Ala
            1635                1640                1645

Ser Gly Thr Asn Val Thr Phe Ala Asp Gly Asn Gly Thr Thr Ala Glu
    1650                1655                1660

Val Thr Lys Ala Asn Asp Gly Ser Ile Thr Val Lys Tyr Asn Val Lys
1665                1670                1675                1680

Val Ala Asp Gly Leu Lys Leu Asp Gly Asp Lys Ile Val Ala Asp Thr
                1685                1690                1695

Thr Val Leu Thr Val Ala Asp Gly Lys Val Thr Ala Pro Asn Asn Gly
            1700                1705                1710

Xaa Gly Lys Lys Phe Xaa Asp Ala Ser Gly Leu Ala Gly Cys Leu Asn
        1715                1720                1725

Lys Leu Ser Xaa Thr Ala Thr Ala Gly Lys Glu Gly Thr Gly Glu Val
        1730                1735                1740

Asp Pro Ala Asn Ser Ala Gly Gln Glu Val Lys Ala Gly Asp Lys Val
1745                1750                1755                1760

Thr Phe Lys Ala Gly Asp Asn Leu Lys Ile Lys Gln Ser Xaa Lys Asp
        1765                1770                1775

Phe Thr Tyr Ser Leu Lys Lys Glu Leu Lys Asp Leu Thr Ser Val Glu
            1780                1785                1790

Phe Lys Asp Ala Asn Gly Gly Thr Gly Ser Glu Ser Thr Lys Ile Thr
        1795                1800                1805

Lys Asp Gly Leu Thr Ile Thr Pro Ala Asn Gly Ala Gly Ala Ala Gly
        1810                1815                1820
```

FIG._4F

```
Ala Asn Thr Ala Asn Thr Ile Ser Val Thr Lys Asp Gly Ile Ser Ala
1825            1830                1835                    1840

Gly Asn Lys Ala Val Thr Asn Val Val Ser Gly Leu Lys Lys Phe Gly
                1845                1850                1855

Asp Gly His Thr Leu Ala Asn Gly Thr Val Ala Asp Phe Glu Lys His
                1860                1865                1870

Tyr Asp Asn Ala Tyr Xaa Asp Leu Thr Asn Leu Asp Glu Xaa Xaa Arg
            1875                1880                1885

Ile Ile Ile Arg Leu Leu Pro Thr Ile Pro Leu Gln Pro Trp Ala Ile
1890                        1895                1900

Xaa Xaa Ala Trp Ala Gly Ser Phe
1905            1910
```

FIG._4G

```
HA2   1 MNKIFNVIWNVMTQTWVVVSELTRTHTKRLRNR.GDPVLATLLFATVQA.  48
        |||||||||||:||||||||||||||||  .. : :|||||| |||:|
HA1   1 MNKIFNVIWNVVTQTWVVVSELTRTHTKCASATVAVAVLATLLSATVEAN  50

49 NATDEDEELDPVVRTAPVLSFHSDKEGTGEKEVTENSNWGIYFDNKG...  95
        |.|. .:.|.:     ..: :.| .:. :.:||:|  |. .  : :::|.
     51 NNTPVTNKLKAY..GDANFNFTNNSIADAEKQVQEAYKGLLNLNEKNASD  98

96 ...VLKAGAITL........................KAGDNLKXKQXTD 117
           | ...| |:                            .|:: |  . .
     99 KLLVEDNTAATVGNLRKLGWVLSSKNGTRNEKSQQVKHADEVLFEGKGGV 148

118 EXTNAS.....SFTYSLKKDLTDLTSVATEKLSFGANGD.......KVDI 155
        : |..|       .:|:.| |||. |.....:.|.:|:.:.     ||::
    149 QVTSTSENGKHTITFALAKDLGVKTATVSDTLTIGGGAAAGATTTPKVNV 198

156 TSDANGLKLAK.....TGNGNVHLNGLDSTLPDAVTNTGVLSSSSFTPND 200
        ||..:|||:||     .|:..||||||::|||.|.:.....   .: ....
    199 TSTTDGLKFAKDAAGANGDTTVHLNGIGSTLTDTLVGSPATHIDG.GDQS 247

201 VEKTRAATVKDVLNAGWNIKGAKTAG..GNVESVDLVSAYNNVEFITGDK 248
        ..  ||||.:||||||||||||.|.::  |. |.||:| .|:.|||:.:|.
    248 THYTRAASIKDVLNAGWNIKGVKAGSTTGQSENVDFVHTYDTVEFLSADT 297

249 NTLDVVLTAKENXKTTEVKFTPKTSVIKEKDGKLFTGKENNDTNKVTSNT 298
        :|  .|..:..||| | ||||:..:||||||||||||||||||.|.:||||.:..
    298 ETTTVTVDSKENGKRTEVKIGAKTSVIKEKDGKLFTGKANKETNKVDGAN 347

299 ATDNTDEGNGLVTAKAVIDAVNKAGWRVKTTTANGQNGDFATVASGTNVT 348
        ||::.|||.||||||.|||||||.|||:|||.||||||||||||||||||
    348 ATEDADEGKGLVTAKDVIDAVNKTGWRIKTTDANGQNGDFATVASGTNVT 397

349 FESGDGTTASVTKDTNGNGITVKYDAKVGDGLKFDSDKKIVADTTALTVT 398
        |.||:||||.||.:|  :|||||||||||||||:|:| ||.||||||||.
    398 FASGNGTTATVTNGT..DGITVKYDAKVGDGLKLDGD.KIAADTTALTVN 444

399 G........GKVAEIAKEDDKKKLVNAGDLVTALGNLSWKAKAEADTDGA 440
        :        ||||::|..|: |||.| :|||||..|||...|....:|.
    445 DGKNANNPKGKVADVASTDE.KKLVTAKGLVTALNSLSWTTTAAEADGGT 493

441 LEGISKDQEVKAGETVTFKAGKNLKVKQDGANFTYSLQDALTGLTSITLG 490
        |:| ..:|||||:.|||||||||||||||:||||||||||||||||||||
    494 LDGNASEQEVKAGDKVTFKAGKNLKVKQEGANFTYSLQDALTGLTSITLG 543

491 GTTNGGNDAKTVINKDGLTITPAGNGGTTGTNTISVTKDGIKAGNKAITN 540
        .  |.|:||| |||||||||..:|....||||||||.||...:.|
    544 T...GNNGAKTEINKDGLTITPANGAGANNANTISVTKDGISAGGQSVKN 590

541 VASGLRAYDDANFDVLNNSATDLNRHVEDAYKGLLNLNEKNANKQ.PLVT 589
        |.|||: ::|||||.|..||.:|.:  :||||||  ||:||..:|| |:|.
    591 VVSGLKKFGDANFDPLTSSADNLTKQNDDAYKGLTNLDEKGTDKQTPVVA 640

590 DSTAATVGDLRKLGWVVS 607
        |.|||||||| ||||:|
    641 DNTAATVGDLRGLGWVIS 658
```

FIG._5

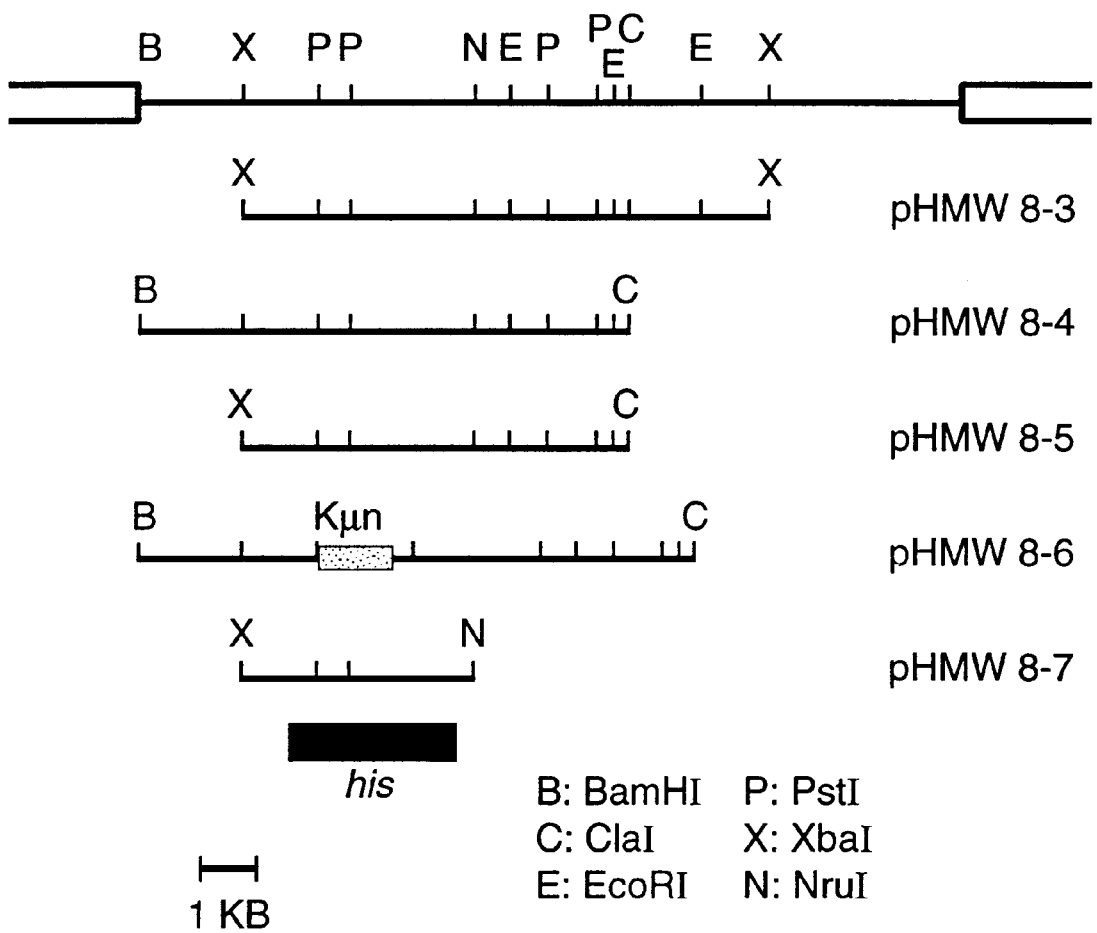
FIG._6

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 3294 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:1:

```
ATGAACAAAA TTTTTAACGT TATTTGGAAT GTTGTGACTC AAACTTGGGT TGTCGTATCT      60

GAACTCACTC GCACCCACAC CAAATGCGCC TCCGCCACCG TGGCGGTTGC CGTATTGGCA     120

ACCCTGTTGT CCGCAACGGT TGAGGCGAAC AACAATACTC CTGTTACGAA TAAGTTGAAG     180

GCTTATGGCG ATGCGAATTT TAATTTCACT AATAATTCGA TAGCAGATGC AGAAAAACAA     240

GTTCAAGAGG CTTATAAAGG TTTATTAAAT CTAAATGAAA AAAATGCGAG TGATAAACTG     300

TTGGTGGAGG ACAATACTGC GGCGACCGTA GGCAATTTGC GTAAATTGGG CTGGGTATTG     360

TCTAGCAAAA ACGGCACAAG GAACGAGAAA AGCCAACAAG TCAAACATGC GGATGAAGTG     420

TTGTTTGAAG GCAAAGGCGG TGTGCAGGTT ACTTCCACCT CTGAAAACGG CAAACACACC     480

ATTACCTTTG CTTTAGCGAA AGACCTTGGT GTGAAAACTG CGACTGTGAG TGATACCTTA     540

ACGATTGGCG GTGGTGCTGC TGCAGGTGCT ACAACAACAC CGAAAGTGAA TGTAACTAGT     600

ACAACTGATG GCTTGAAGTT CGCTAAAGAT GCTGCGGGTG CTAATGGCGA TACTACGGTT     660

CACTTGAATG GTATTGGTTC AACCTTGACA GACACGCTTG TGGGTTCTCC TGCTACTCAT     720

ATTGACGGAG GAGATCAAAG TACGCATTAC ACTCGTGCAG CAAGTATCAA GGATGTCTTG     780

AATGCGGGTT GGAATATCAA GGGTGTTAAA GCTGGCTCAA CAACTGGTCA ATCAGAAAAT     840

GTCGATTTTG TTCATACTTA CGATACTGTT GAGTTCTTGA GTGCGGATAC AGAGACCACG     900
```

```
ACTGTTACTG TAGATAGCAA AGAAAACGGT AAGAGAACCG AAGTTAAAAT CGGTGCGAAG      960

ACTTCTGTTA TCAAAGAAAA AGACGGTAAG TTATTTACTG GAAAAGCTAA CAAAGAGACA     1020

AATAAAGTTG ATGGTGCTAA CGCGACTGAA GATGCAGACG AAGGCAAAGG CTTAGTGACT     1080

GCGAAAGATG TGATTGACGC AGTGAATAAG ACTGGTTGGA GAATTAAAAC AACCGATGCT     1140

AATGGTCAAA ATGGCGACTT CGCAACTGTT GCATCAGGCA CAAATGTAAC CTTTGCTAGT     1200

GGTAATGGTA CAACTGCGAC TGTAACTAAT GGCACCGATG GTATTACCGT TAAGTATGAT     1260

GCGAAAGTTG GCGACGGCTT AAAACTAGAT GGCGATAAAA TCGCTGCAGA TACGACCGCA     1320

CTTACTGTGA ATGATGGTAA GAACGCTAAT AATCCGAAAG GTAAAGTGGC TGATGTTGCT     1380

TCAACTGACG AGAAGAAATT GGTTACAGCA AAAGGTTTAG TAACAGCCTT AAACAGTCTA     1440

AGCTGGACTA CAACTGCTGC TGAGGCGGAC GGTGGTACGC TTGATGGAAA TGCAAGTGAG     1500

CAAGAAGTTA AAGCGGGCGA TAAAGTAACC TTTAAAGCAG GCAAGAACTT AAAAGTGAAA     1560

CAAGAGGGTG CGAACTTTAC TTATTCACTG CAAGATGCTT TAACAGGCTT AACGAGCATT     1620

ACTTTAGGTA CAGGAAATAA TGGTGCGAAA ACTGAAATCA ACAAAGACGG CTTAACCATC     1680

ACACCAGCAA ATGGTGCGGG TGCAAATAAT GCAAACACCA TCAGCGTAAC CAAAGACGGC     1740

ATTAGTGCGG GCGGTCAGTC GGTTAAAAAC GTTGTGAGCG GACTGAAGAA ATTTGGTGAT     1800

GCGAATTTCG ATCCGCTGAC TAGCTCCGCC GACAACTTAA CGAAACAAAA TGACGATGCC     1860

TATAAAGGCT TGACCAATTT GGATGAAAAA GGTACAGACA AGCAAACTCC AGTTGTTGCC     1920

GACAATACCG CCGCAACCGT GGGCGATTTG CGCGGCTTGG GCTGGGTCAT TTCTGCGGAC     1980

AAAACCACAG GCGGCTCAAC GGAATATCAC GATCAAGTTC GGAATGCGAA CGAAGTGAAA     2040

TTCAAAAGCG GCAACGGTAT CAATGTTTCC GGTAAAACGG TCAACGGTAG GCGTGAAATT     2100

ACTTTTGAAT TGGCTAAAGG TGAAGTGGTT AAATCGAATG AATTTACCGT CAAAGAAACC     2160

AATGGAAAGG AAACGAGCCT GGTTAAAGTT GGCGATAAAT ATTACAGCAA AGAGGATATT     2220

GACTTAACAA CAGGTCAGCC TAAATTAAAA GATGGCAATA CAGTTGCTGC GAAATATCAA     2280

GATAAAGGTG GCAAAGTCGT TTCTGTAACG GATAATACTG AAGCTACCAT AACCAACAAA     2340

GGTTCTGGCT ATGTAACAGG TAACCAAGTG GCAGATGCGA TTGCGAAATC AGGCTTTGAG     2400

CTTGGCTTGG CTGATGAAGC TGATGCGAAA CGGGCGTTTG ATGATAAGAC AAAAGCCTTA     2460

TCTGCTGGTA CAACGGAAAT TGTAAATGCC CACGATAAAG TCCGTTTTGC TAATGGTTTA     2520

AATACCAAAG TGAGCGCGGC AACGGTGGAA AGCACCGATG CAAACGGCGA TAAAGTGACC     2580

ACAACCTTTG TGAAAACCGA TGTGGAATTG CCTTTAACGC AAATCTACAA TACCGATGCA     2640

AACGGTAAGA AAATCACTAA AGTTGTCAAA GATGGGCAAA CTAAATGGTA TGAACTGAAT     2700

GCTGACGGTA CGGCTGATAT GACCAAAGAA GTTACCCTCG GTAACGTGGA TTCAGACGGC     2760

AAGAAAGTTG TGAAAGACAA CGATGGCAAG TGGTATCACG CCAAAGCTGA CGGTACTGCG     2820

GATAAAACCA AAGGCGAAGT GAGCAATGAT AAAGTTTCTA CCGATGAAAA ACACGTTGTC     2880

AGCCTTGATC CAAATGATCA ATCAAAAGGT AAAGGTGTCG TGATTGACAA TGTGGCTAAT     2940

GGCGATATTT CTGCCACTTC CACCGATGCG ATTAACGGAA GTCAGTTGTA TGCTGTGGCA     3000

AAAGGGGTAA CAAACCTTGC TGGACAAGTG AATAATCTTG AGGGCAAAGT GAATAAAGTG     3060

GGCAAACGTG CAGATGCAGG TACAGCAAGT GCATTAGCGG CTTCACAGTT ACCACAAGCC     3120

ACTATGCCAG GTAAATCAAT GGTTGCTATT GCGGGAAGTA GTTATCAAGG TCAAAATGGT     3180

TTAGCTATCG GGGTATCAAG AATTTCCGAT AATGGCAAAG TGATTATTCG CTTGTCAGGC     3240

ACAACCAATA GTCAAGGTAA AACAGGCGTT GCAGCAGGTG TTGGTTACCA GTGG          3294
```

(2) INFORMATION FOR SEQ ID NO:2:

(i) SEQUENCE CHARACTERISTICS:
        (A) LENGTH: 1098 amino acids
        (B) TYPE: amino acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:2:

```
Met Asn Lys Ile Phe Asn Val Ile Trp Asn Val Val Thr Gln Thr Trp
  1               5                  10                  15

Val Val Val Ser Glu Leu Thr Arg Thr His Thr Lys Cys Ala Ser Ala
             20                  25                  30

Thr Val Ala Val Ala Val Leu Ala Thr Leu Leu Ser Ala Thr Val Glu
         35                  40                  45

Ala Asn Asn Asn Thr Pro Val Thr Asn Lys Leu Lys Ala Tyr Gly Asp
     50                  55                  60

Ala Asn Phe Asn Phe Thr Asn Asn Ser Ile Ala Asp Ala Glu Lys Gln
 65                  70                  75                  80

Val Gln Glu Ala Tyr Lys Gly Leu Leu Asn Leu Asn Glu Lys Asn Ala
                 85                  90                  95

Ser Asp Lys Leu Leu Val Glu Asp Asn Thr Ala Ala Thr Val Gly Asn
            100                 105                 110

Leu Arg Lys Leu Gly Trp Val Leu Ser Ser Lys Asn Gly Thr Arg Asn
            115                 120                 125

Glu Lys Ser Gln Gln Val Lys His Ala Asp Glu Val Leu Phe Glu Gly
        130                 135                 140

Lys Gly Gly Val Gln Val Thr Ser Thr Ser Glu Asn Gly Lys His Thr
145                 150                 155                 160

Ile Thr Phe Ala Leu Ala Lys Asp Leu Gly Val Lys Thr Ala Thr Val
                165                 170                 175

Ser Asp Thr Leu Thr Ile Gly Gly Ala Ala Ala Gly Ala Thr Thr
            180                 185                 190

Thr Pro Lys Val Asn Val Thr Ser Thr Asp Gly Leu Lys Phe Ala
            195                 200                 205

Lys Asp Ala Ala Gly Ala Asn Gly Asp Thr Thr Val His Leu Asn Gly
            210                 215                 220

Ile Gly Ser Thr Leu Thr Asp Thr Leu Val Gly Ser Pro Ala Thr His
225                 230                 235                 240

Ile Asp Gly Gly Asp Gln Ser Thr His Tyr Thr Arg Ala Ala Ser Ile
                245                 250                 255

Lys Asp Val Leu Asn Ala Gly Trp Asn Ile Lys Gly Val Lys Ala Gly
            260                 265                 270

Ser Thr Thr Gly Gln Ser Glu Asn Val Asp Phe Val His Thr Tyr Asp
        275                 280                 285

Thr Val Glu Phe Leu Ser Ala Asp Thr Glu Thr Thr Val Thr Val
            290                 295                 300

Asp Ser Lys Glu Asn Gly Lys Arg Thr Glu Val Lys Ile Gly Ala Lys
305                 310                 315                 320

Thr Ser Val Ile Lys Glu Lys Asp Gly Lys Leu Phe Thr Gly Lys Ala
                325                 330                 335

Asn Lys Glu Thr Asn Lys Val Asp Gly Ala Asn Ala Thr Glu Asp Ala
            340                 345                 350
```

-continued

```
Asp Glu Gly Lys Gly Leu Val Thr Ala Lys Asp Val Ile Asp Ala Val
            355                 360                 365
Asn Lys Thr Gly Trp Arg Ile Lys Thr Thr Asp Ala Asn Gly Gln Asn
        370                 375                 380
Gly Asp Phe Ala Thr Val Ala Ser Gly Thr Asn Val Thr Phe Ala Ser
385                 390                 395                 400
Gly Asn Gly Thr Thr Ala Thr Val Thr Asn Gly Thr Asp Gly Ile Thr
                405                 410                 415
Val Lys Tyr Asp Ala Lys Val Gly Asp Gly Leu Lys Leu Asp Gly Asp
            420                 425                 430
Lys Ile Ala Ala Asp Thr Thr Ala Leu Thr Val Asn Asp Gly Lys Asn
        435                 440                 445
Ala Asn Asn Pro Lys Gly Lys Val Ala Asp Val Ala Ser Thr Asp Glu
    450                 455                 460
Lys Lys Leu Val Thr Ala Lys Gly Leu Val Thr Ala Leu Asn Ser Leu
465                 470                 475                 480
Ser Trp Thr Thr Thr Ala Ala Glu Ala Asp Gly Gly Thr Leu Asp Gly
                485                 490                 495
Asn Ala Ser Glu Gln Glu Val Lys Ala Gly Asp Lys Val Thr Phe Lys
            500                 505                 510
Ala Gly Lys Asn Leu Lys Val Lys Gln Glu Gly Ala Asn Phe Thr Tyr
        515                 520                 525
Ser Leu Gln Asp Ala Leu Thr Gly Leu Thr Ser Ile Thr Leu Gly Thr
    530                 535                 540
Gly Asn Asn Gly Ala Lys Thr Glu Ile Asn Lys Asp Gly Leu Thr Ile
545                 550                 555                 560
Thr Pro Ala Asn Gly Ala Gly Ala Asn Asn Ala Asn Thr Ile Ser Val
                565                 570                 575
Thr Lys Asp Gly Ile Ser Ala Gly Gly Gln Ser Val Lys Asn Val Val
            580                 585                 590
Ser Gly Leu Lys Lys Phe Gly Asp Ala Asn Phe Asp Pro Leu Thr Ser
        595                 600                 605
Ser Ala Asp Asn Leu Thr Lys Gln Asn Asp Asp Ala Tyr Lys Gly Leu
    610                 615                 620
Thr Asn Leu Asp Glu Lys Gly Thr Asp Lys Gln Thr Pro Val Val Ala
625                 630                 635                 640
Asp Asn Thr Ala Ala Thr Val Gly Asp Leu Arg Gly Leu Gly Trp Val
                645                 650                 655
Ile Ser Ala Asp Lys Thr Thr Gly Gly Ser Thr Glu Tyr His Asp Gln
            660                 665                 670
Val Arg Asn Ala Asn Glu Val Lys Phe Lys Ser Gly Asn Gly Ile Asn
        675                 680                 685
Val Ser Gly Lys Thr Val Asn Gly Arg Arg Glu Ile Thr Phe Glu Leu
    690                 695                 700
Ala Lys Gly Glu Val Val Lys Ser Asn Glu Phe Thr Val Lys Glu Thr
705                 710                 715                 720
Asn Gly Lys Glu Thr Ser Leu Val Lys Val Gly Asp Lys Tyr Tyr Ser
                725                 730                 735
Lys Glu Asp Ile Asp Leu Thr Thr Gly Gln Pro Lys Leu Lys Asp Gly
            740                 745                 750
Asn Thr Val Ala Ala Lys Tyr Gln Asp Lys Gly Gly Lys Val Val Ser
        755                 760                 765
```

```
Val Thr Asp Asn Thr Glu Ala Thr Ile Thr Asn Lys Gly Ser Gly Tyr
    770                 775                 780

Val Thr Gly Asn Gln Val Ala Asp Ala Ile Ala Lys Ser Gly Phe Glu
785                 790                 795                 800

Leu Gly Leu Ala Asp Glu Ala Asp Ala Lys Arg Ala Phe Asp Asp Lys
                805                 810                 815

Thr Lys Ala Leu Ser Ala Gly Thr Thr Glu Ile Val Asn Ala His Asp
            820                 825                 830

Lys Val Arg Phe Ala Asn Gly Leu Asn Thr Lys Val Ser Ala Ala Thr
        835                 840                 845

Val Glu Ser Thr Asp Ala Asn Gly Asp Lys Val Thr Thr Thr Phe Val
    850                 855                 860

Lys Thr Asp Val Glu Leu Pro Leu Thr Gln Ile Tyr Asn Thr Asp Ala
865                 870                 875                 880

Asn Gly Lys Lys Ile Thr Lys Val Val Lys Asp Gly Gln Thr Lys Trp
                885                 890                 895

Tyr Glu Leu Asn Ala Asp Gly Thr Ala Asp Met Thr Lys Glu Val Thr
            900                 905                 910

Leu Gly Asn Val Asp Ser Asp Gly Lys Lys Val Val Lys Asp Asn Asp
        915                 920                 925

Gly Lys Trp Tyr His Ala Lys Ala Asp Gly Thr Ala Asp Lys Thr Lys
    930                 935                 940

Gly Glu Val Ser Asn Asp Lys Val Ser Thr Asp Glu Lys His Val Val
945                 950                 955                 960

Ser Leu Asp Pro Asn Asp Gln Ser Lys Gly Lys Gly Val Val Ile Asp
                965                 970                 975

Asn Val Ala Asn Gly Asp Ile Ser Ala Thr Ser Thr Asp Ala Ile Asn
            980                 985                 990

Gly Ser Gln Leu Tyr Ala Val Ala Lys Gly Val Thr Asn Leu Ala Gly
        995                 1000                1005

Gln Val Asn Asn Leu Glu Gly Lys Val Asn Lys Val Gly Lys Arg Ala
    1010                1015                1020

Asp Ala Gly Thr Ala Ser Ala Leu Ala Ala Ser Gln Leu Pro Gln Ala
1025                1030                1035                1040

Thr Met Pro Gly Lys Ser Met Val Ala Ile Ala Gly Ser Ser Tyr Gln
                1045                1050                1055

Gly Gln Asn Gly Leu Ala Ile Gly Val Ser Arg Ile Ser Asp Asn Gly
            1060                1065                1070

Lys Val Ile Ile Arg Leu Ser Gly Thr Thr Asn Ser Gln Gly Lys Thr
        1075                1080                1085

Gly Val Ala Ala Gly Val Gly Tyr Gln Trp
    1090                1095

(2) INFORMATION FOR SEQ ID NO:3:

(i) SEQUENCE CHARACTERISTICS:
        (A) LENGTH: 5738 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:3:

ATGAACAAAA TTTTTAACGT TATTTGGAAT GTTATGACTC AAACTTGGGT TGTCGTATCT      60

GAACTCACTC GCACCCACAC CAAACGCCTC CGCAACCGTG GAGACCCCGT ATTGGCGACA     120
```

```
CTGTTGTTTG CAACGGTTCA GGCGAATGCT ACCGATGAAG ATGAAGAGTT AGACCCCGTA       180
GTACGCACTG CTCCCGTGTT GAGCTTCCAT TCCGATAAAG AAGGCACGGG AGAAAAAGAA       240
GTTACAGAAA ATTCAAATTG GGAATATATT TTCGACAATA AAGGAGTACT AAAAGCCGGA       300
GCAATCACCC TCAAAGCCGG CGACAACCTG AAAATNAAAC AAAANACCGA TGAAAGNACC       360
AATGCCAGTA GCTTCACCTA CTCGCTGAAA AAAGACCTCA CAGATCTGAC CAGTGTTGCA       420
ACTGAAAAAT TATCGTTTGG CGCAAACGGC GATAAAGTTG ATATTACCAG TGATGCAAAT       480
GGCTTGAAAT TGGCGAAAAC AGGTAACGGA AATGTTCATT TGAATGGTTT GGATTCAACT       540
TTGCCTGATG CGGTAACGAA TACAGGTGTG TTAAGTTCAT CAAGTTTTAC ACCTAATGAT       600
GTTGAAAAAA CAAGAGCTGC AACTGTTAAA GATGTTTTAA ATGCAGGTTG GAACATTAAA       660
GGTGCTAAAA CTGCTGGAGG TAATGTTGAG AGTGTTGATT TAGTGTCCGC TTATAATAAT       720
GTTGAATTTA TTACAGGCGA TAAAAACACG CTTGATGTTG TATTAACAGC TAAAGAAAAC       780
NGTAAAACAA CCGAAGTGAA ATTCACACCG AAAACCTCTG TTATCAAAGA AAAAGACGGT       840
AAGTTATTTA CTGAAAAAGA GAATAACGAC ACAAATAAAG TTACAAGTAA CACGGCGACT       900
GATAATACAG ATGAGGGTAA TGGCTTAGTC ACTGCAAAAG CTGTGATTGA TGCTGTGAAC       960
AAGGCTGGTT GGAGAGTTAA AACAACTACT GCTAATGGTC AAAATGGCGA CTTCGCAACT      1020
GTTGCGTCAG GCACAAATGT AACCTTTGAA AGTGGCGATG GTACAACAGC GTCAGTAACT      1080
AAAGATACTA ACGGCAATGG CATCACTGTT AAGTACGACG CGAAAGTTGG CGACGGCTTG      1140
AAATTTGATA GCGATAAAAA AATCGTTGCA GATACGACCG CACTTACTGT GACAGGTGGT      1200
AAGGTAGCTG AAATTGCTAA AGAAGATGAC AAGAAAAAAC TTGTTAATGC AGGCGATTTG      1260
GTAACAGCTT TAGGTAATCT AAGTTGGAAA GCAAAGCTG AGGCTGATAC TGATGGTGCG       1320
CTTGAGGGGA TTTCAAAAGA CCAAGAAGTC AAAGCAGGCG AAACGGTAAC CTTTAAAGCG      1380
GGCAAGAACT TAAAAGTGAA ACAGGATGGT GCGAACTTTA CTTATTCACT GCAAGATGCT      1440
TTAACGGGTT TAACGAGCAT TACTTTAGGT GGTACAACTA ATGGCGGAAA TGATGCGAAA      1500
ACCGTCATCA ACAAAGACGG TTTAACCATC ACGCCAGCAG GTAATGGCGG TACGACAGGT      1560
ACAAACACCA TCAGCGTAAC CAAAGATGGC ATTAAAGCAG GTAATAAAGC TATTACTAAT      1620
GTTGCGAGTG GGTTAAGAGC TTATGACGAT GCGAATTTTG ATGTTTTAAA TAACTCTGCA      1680
ACTGATTTAA ATAGACACGT TGAAGATGCT TATAAAGGTT TATTAAATCT AAATGAAAAA      1740
AATGCAAATA AACAACCGTT GGTGACTGAC AGCACGGCGG CGACTGTAGG CGATTTACGT      1800
AAATTGGGTT GGGTAGTATC AACCAAAAAC GGTACGAAAG AAGAAAGCAA TCAAGTTAAA      1860
CAAGCTGATG AAGTCCTCTT TACCGGAGCC GGTGCTGCTA CGGTTACTTC CAAATCTGAA      1920
AACGGTAAAC ATACGATTAC CGTTAGTGTG GCTGAAACTA AAGCGGATTG CGGTCTTGAA      1980
AAAGATGGCG ATACTATTAA GCTCAAAGTG GATAATCAAA CACTGATAA TGTTTTAACT      2040
GTTGGTAATA ATGGTACTGC TGTCACTAAA GGTGGCTTTG AAACTGTTAA AACTGGAGCG      2100
ACTGATGCAG ATCGCGGTAA AGTAACTGTA AAAGATGCTA CTGCTAATGA CGCTGATAAG      2160
AAAGTCGCAA CTGTAAAAGA TGTTGCAACC GCAATTAATA GTGCGGCGAC TTTTGTGAAA      2220
ACAGAGAATT TAACTACCTC TATTGATGAA GATAATCCTA CAGATAACGG CAAAGATGAC      2280
GCACTTAAAG CGGGCGATAC CTTAACCTTT AAAGCAGGTA AAAACCTGAA AGTTAAACGT      2340
GATGGAAAAA ATATTACTTT TGACTTGGCN AAAAACCTTG AGGTGAAAAC TGCGAAAGTG      2400
AGTGATACTT TAACGATTGG CGGGAATACA CCTACAGGTG GCACTACTGC GACGCCAAAA      2460
```

```
GTGAATATTA CTAGCACGGC TGATGGTTTG AATTTTGCAA AGAAACAGC CGATGCCTCG    2520

GGTTCTAAGA ATGTTTATTT GAAAGGTATT GCGACAACTT AACTGAGCC AAGCGCGGGA    2580

GCGAAGTCTT CACACGTTGA TTTAAATGTG GATGCGACGA AAAAATCCAA TGCAGCAAGT    2640

ATTGAAGATG TATTGCGCGC AGGTTGGAAT ATTCAAGGTA ATGGTAATAA TGTTGATTAT    2700

GTAGCGACGT ATGACACAGT AAACTTTACC GATGACAGCA CAGGTACAAC AACGGTAACC    2760

GTAACCCAAA AAGCAGATGG CAAAGGTGCT GACGTTAAAA TCGGTGCGAA AACTTCTGTT    2820

ATCAAAGACC ACAACGGCAA ACTGTTTACA GGCAAAGACC TGAAAGATGC GAATAATGGT    2880

GCAACCGTTA GTGAAGATGA TGGCAAAGAC ACCGGCACAG GCTTAGTTAC TGCAAAAACT    2940

GTGATTGATG CAGTAAATAA AAGCGGTTGG AGGGTAACCG TGAGGGCGC GACTGCCGAA    3000

ACCGGTGCAA CCGCCGTGAA TGCGGGTAAC GCTGAAACCG TTACATCAGG CACGAGCGTG    3060

AACTTCAAAA ACGGCAATGC GACCACAGCG ACCGTAAGCA AAGATAATGG CAACATCAAT    3120

GTCAAATACG ATGTAAATGT TGGTGACGGC TTGAAGATTG GCGATGACAA AAAAATCGTT    3180

GCAGACACGA CCACACTTAC TGTAACAGGT GGTAAGGTGT CTGTTCCTGC TGGTGCTAAT    3240

AGTGTTAATA ACAATAAGAA ACTTGTTAAT GCAGAGGGTT TAGCGACTGC TTTAAACAAC    3300

CTAAGCTGGA CGGCAAAAGC CGATAAATAT GCAGATGGCG AGTCAGAGGG CGAAACCGAC    3360

CAAGAAGTCA AAGCAGGCGA CAAAGTAACC TTTAAAGCAG GCAAGAACTT AAAAGTGAAA    3420

CAGTCTGAAA AAGACTTTAC TTATTCACTG CAAGACACTT TAACAGGCTT AACGAGCATT    3480

ACTTTAGGTG GTACAGCTAA TGGCAGAAAT GATACGGGAA CCGTCATCAA CAAAGACGGC    3540

TTAACCATCA CGCTGGCAAA TGGTGCTGCG GCAGGCACAG ATGCGTCTAA CGGAAACACC    3600

ATCAGTGTAA CCAAAGACGG CATTAGTGCG GGTAATAAAG AAATTACCAA TGTTAAGAGT    3660

GCTTTAAAAA CCTATAAAGA TACTCAAAAC ACTGCAGATG AAACAAGA TAAAGAGTTC     3720

CACGCCGCCG TTAAAAACGC AAATGAAGTT GAGTTCGTGG GTAAAAACGG TGCAACCGTG    3780

TCTGCAAAAA CTGATAACAA CGGAAAACAT ACTGTAACGA TTGATGTTGC AGAAGCCAAA    3840

GTTGGTGATG GTCTTGAAAA AGATACTGAC GGCAAGATTA AACTCAAAGT AGATAATACA    3900

GATGGGAATA ATCTATTAAC CGTTGATGCA ACAAAAGGTG CATCCGTTGC CAAGGGCGAG    3960

TTTAATGCCG TAACAACAGA TGCAACTACA GCCCAAGGCA CAAATGCCAA TGAGCGCGGT    4020

AAAGTGGTTG TCAAGGGTTC AAATGGTGCA ACTGCTACCG AAACTGACAA GAAAAAAGTG    4080

GCAACTGTTG GCGACGTTGC TAAAGCGATT AACGACGCAG CAACTTTCGT GAAAGTGGAA    4140

AATGACGACA GTGCTACGAT TGATGATAGC CCAACAGATG ATGGCGCAAA TGATGCTCTC    4200

AAAGCANGCG ACACCTTGAC CTTAAAAGCG GGTAAAAACT TAAAAGTTAA ACGTGATGGT    4260

AAAAATATTA CTTTTGCCCT TGCGAACGAC CTTAGTGTAA AAAGCGCAAC CGTTAGCGAT    4320

AAATTATCGC TTGGTACAAA CGGCAATAAA GTCAATATCA CAAGCGACAC CAAAGGCTTG    4380

AACTTCGCTA AAGATAGTAA GACAGGCGAT GATGCTAATA TTCACTTAAA TGGCATTGCT    4440

TCAACTTTAA CTGATACATT GTTAAATAGT GGTGCGACAA CCAATTTAGG TGGTAATGGT    4500

ATTACTGATA ACGAGAAAAA ANNCGCGGCG AGCGTTAAAG ATGTCTTGAA TGCGGGTTGG    4560

AATGTTCGTG GTGTTAAACC GGCATCTGCA AATAATCAAG TGGAGAATAT CGACTTTGTA    4620

GCAACCTACG ACACAGTGGA CTTTGTTAGT GGAGATAAAG ACACCACGAG TGTAACTGTT    4680

GAAAGTAAAG ATAATGGCAA GAGAACCGAA GTTAAAATCG GTGCGAAGAC TTCTGTTATC    4740

AAAGACCACA ACGGCAAACT GTTTACAGGC AAAGAGCTGA AGGATGCTAA CAATAATGGC    4800

GTAACTGTTA CCGAAACCGA CGGCAAAGAC GAGGGTAATG GTTTAGTGAC TGCAAAAGCT    4860
```

-continued

```
GTGATTGATG CCGTGAATAA GGCTGGTTGG AGAGTTAAAA CAACAGGTGC TAATGGTCAG    4920

AATGATGACT TCGCAACTGT TGCGTCAGGC ACAAATGTAA CCTTTGCTGA TGGTAATGGC    4980

ACAACTGCCG AAGTAACTAA AGCAAACGAC GGTAGTATTA CTGTTAAATA CAATGTTAAA    5040

GTGGCTGATG GCTTAAAACT AGACGGCGAT AAAATCGTTG CAGACACGAC CGTACTTACT    5100

GTGGCAGATG GTAAAGTTAC AGCTCCGAAT AATGGCNATG GTAAGAAATT TNTTGATGCA    5160

AGTGGTTTAG CGGGATGCTT AAATAAATTA AGCTNGACGG CAACTGCTGG TAAAGAAGGC    5220

ACTGGTGAAG TTGATCCTGC AAATTCAGCA GGGCAAGAAG TCAAAGCGGG CGACAAAGTA    5280

ACCTTTAAAG CCGGCGACAA CCTGAAAATC AAACAAAGCG NCAAAGACTT TACCTACTCG    5340

CTGAAAAAAG AGCTGAAAGA CCTGACCAGC GTAGAGTTCA AGACGCAAA CGGCGGTACA     5400

GGCAGTGAAA GCACCAAGAT TACCAAAGAC GGCTTGACCA TTACGCCGGC AAACGGTGCG    5460

GGTGCGGCAG GTGCAAACAC TGCAAACACC ATTAGCGTAA CCAAAGATGG CATTAGCGCG    5520

GGTAATAAAG CAGTTACAAA CGTTGTGAGC GGACTGAAGA AATTTGGTGA TGGTCATACG    5580

TTGGCAAATG GCACTGTTGC TGATTTTGAA AAGCATTATG ACAATGCCTA TAANGACTTG    5640

ACCAATTTGG ATGAANANNC NCGGATAATA ATCCGACTGT TGCCGACAAT ACCGCTGCAA    5700

CCGTGGGCGA TTTNNNNGGC TTGGGCTGGG TCATTTCT                            5738
```

(2) INFORMATION FOR SEQ ID NO:4:

(i) SEQUENCE CHARACTERISTICS:
        (A) LENGTH: 1912 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:4:

```
Met Asn Lys Ile Phe Asn Val Ile Trp Asn Val Met Thr Gln Thr Trp
 1               5                  10                  15

Val Val Val Ser Glu Leu Thr Arg Thr His Thr Lys Arg Leu Arg Asn
            20                  25                  30

Arg Gly Asp Pro Val Leu Ala Thr Leu Leu Phe Ala Thr Val Gln Ala
        35                  40                  45

Asn Ala Thr Asp Glu Asp Glu Glu Leu Asp Pro Val Val Arg Thr Ala
    50                  55                  60

Pro Val Leu Ser Phe His Ser Asp Lys Glu Gly Thr Gly Glu Lys Glu
65                  70                  75                  80

Val Thr Glu Asn Ser Asn Trp Gly Ile Tyr Phe Asp Asn Lys Gly Val
                85                  90                  95

Leu Lys Ala Gly Ala Ile Thr Leu Lys Ala Gly Asp Asn Leu Lys Xaa
            100                 105                 110

Lys Gln Xaa Thr Asp Glu Xaa Thr Asn Ala Ser Ser Phe Thr Tyr Ser
        115                 120                 125

Leu Lys Lys Asp Leu Thr Asp Leu Thr Ser Val Ala Thr Glu Lys Leu
    130                 135                 140

Ser Phe Gly Ala Asn Gly Asp Lys Val Asp Ile Thr Ser Asp Ala Asn
145                 150                 155                 160

Gly Leu Lys Leu Ala Lys Thr Gly Asn Gly Asn Val His Leu Asn Gly
                165                 170                 175

Leu Asp Ser Thr Leu Pro Asp Ala Val Thr Asn Thr Gly Val Leu Ser
            180                 185                 190
```

-continued

```
Ser Ser Ser Phe Thr Pro Asn Asp Val Glu Lys Thr Arg Ala Ala Thr
            195                 200                 205

Val Lys Asp Val Leu Asn Ala Gly Trp Asn Ile Lys Gly Ala Lys Thr
210                 215                 220

Ala Gly Gly Asn Val Glu Ser Val Asp Leu Val Ser Ala Tyr Asn Asn
225                 230                 235                 240

Val Glu Phe Ile Thr Gly Asp Lys Asn Thr Leu Asp Val Val Leu Thr
                245                 250                 255

Ala Lys Glu Asn Xaa Lys Thr Thr Glu Val Lys Phe Thr Pro Lys Thr
            260                 265                 270

Ser Val Ile Lys Glu Lys Asp Gly Lys Leu Phe Thr Gly Lys Glu Asn
            275                 280                 285

Asn Asp Thr Asn Lys Val Thr Ser Asn Thr Ala Thr Asp Asn Thr Asp
290                 295                 300

Glu Gly Asn Gly Leu Val Thr Ala Lys Ala Val Ile Asp Ala Val Asn
305                 310                 315                 320

Lys Ala Gly Trp Arg Val Lys Thr Thr Thr Ala Asn Gly Gln Asn Gly
                325                 330                 335

Asp Phe Ala Thr Val Ala Ser Gly Thr Asn Val Thr Phe Glu Ser Gly
            340                 345                 350

Asp Gly Thr Thr Ala Ser Val Thr Lys Asp Thr Asn Gly Asn Gly Ile
            355                 360                 365

Thr Val Lys Tyr Asp Ala Lys Val Gly Asp Gly Leu Lys Phe Asp Ser
            370                 375                 380

Asp Lys Lys Ile Val Ala Asp Thr Thr Ala Leu Thr Val Thr Gly Gly
385                 390                 395                 400

Lys Val Ala Glu Ile Ala Lys Glu Asp Asp Lys Lys Leu Val Asn
                405                 410                 415

Ala Gly Asp Leu Val Thr Ala Leu Gly Asn Leu Ser Trp Lys Ala Lys
            420                 425                 430

Ala Glu Ala Asp Thr Asp Gly Ala Leu Glu Gly Ile Ser Lys Asp Gln
            435                 440                 445

Glu Val Lys Ala Gly Glu Thr Val Thr Phe Lys Ala Gly Lys Asn Leu
450                 455                 460

Lys Val Lys Gln Asp Gly Ala Asn Phe Thr Tyr Ser Leu Gln Asp Ala
465                 470                 475                 480

Leu Thr Gly Leu Thr Ser Ile Thr Leu Gly Gly Thr Thr Asn Gly Gly
                485                 490                 495

Asn Asp Ala Lys Thr Val Ile Asn Lys Asp Gly Leu Thr Ile Thr Pro
            500                 505                 510

Ala Gly Asn Gly Gly Thr Thr Gly Thr Asn Thr Ile Ser Val Thr Lys
            515                 520                 525

Asp Gly Ile Lys Ala Gly Asn Lys Ala Ile Thr Asn Val Ala Ser Gly
            530                 535                 540

Leu Arg Ala Tyr Asp Asp Ala Asn Phe Asp Val Leu Asn Asn Ser Ala
545                 550                 555                 560

Thr Asp Leu Asn Arg His Val Glu Asp Ala Tyr Lys Gly Leu Leu Asn
                565                 570                 575

Leu Asn Glu Lys Asn Ala Asn Lys Gln Pro Leu Val Thr Asp Ser Thr
            580                 585                 590

Ala Ala Thr Val Gly Asp Leu Arg Lys Leu Gly Trp Val Val Ser Thr
            595                 600                 605
```

-continued

```
Lys Asn Gly Thr Lys Glu Glu Ser Asn Gln Val Lys Gln Ala Asp Glu
    610                 615                 620
Val Leu Phe Thr Gly Ala Gly Ala Ala Thr Val Thr Ser Lys Ser Glu
625                 630                 635                 640
Asn Gly Lys His Thr Ile Thr Val Ser Val Ala Glu Thr Lys Ala Asp
                645                 650                 655
Cys Gly Leu Glu Lys Asp Gly Asp Thr Ile Lys Leu Lys Val Asp Asn
                660                 665                 670
Gln Asn Thr Asp Asn Val Leu Thr Val Gly Asn Asn Gly Thr Ala Val
            675                 680                 685
Thr Lys Gly Gly Phe Glu Thr Val Lys Thr Gly Ala Thr Asp Ala Asp
        690                 695                 700
Arg Gly Lys Val Thr Val Lys Asp Ala Thr Ala Asn Asp Ala Asp Lys
705                 710                 715                 720
Lys Val Ala Thr Val Lys Asp Val Ala Thr Ala Ile Asn Ser Ala Ala
                725                 730                 735
Thr Phe Val Lys Thr Glu Asn Leu Thr Thr Ser Ile Asp Glu Asp Asn
                740                 745                 750
Pro Thr Asp Asn Gly Lys Asp Asp Ala Leu Lys Ala Gly Asp Thr Leu
            755                 760                 765
Thr Phe Lys Ala Gly Lys Asn Leu Lys Val Lys Arg Asp Gly Lys Asn
        770                 775                 780
Ile Thr Phe Asp Leu Ala Lys Asn Leu Glu Val Lys Thr Ala Lys Val
785                 790                 795                 800
Ser Asp Thr Leu Thr Ile Gly Gly Asn Thr Pro Thr Gly Gly Thr Thr
                805                 810                 815
Ala Thr Pro Lys Val Asn Ile Thr Ser Thr Ala Asp Gly Leu Asn Phe
            820                 825                 830
Ala Lys Glu Thr Ala Asp Ala Ser Gly Ser Lys Asn Val Tyr Leu Lys
        835                 840                 845
Gly Ile Ala Thr Thr Leu Thr Glu Pro Ser Ala Gly Ala Lys Ser Ser
850                 855                 860
His Val Asp Leu Asn Val Asp Ala Thr Lys Lys Ser Asn Ala Ala Ser
865                 870                 875                 880
Ile Glu Asp Val Leu Arg Ala Gly Trp Asn Ile Gln Gly Asn Gly Asn
                885                 890                 895
Asn Val Asp Tyr Val Ala Thr Tyr Asp Thr Val Asn Phe Thr Asp Asp
            900                 905                 910
Ser Thr Gly Thr Thr Thr Val Thr Val Thr Gln Lys Ala Asp Gly Lys
        915                 920                 925
Gly Ala Asp Val Lys Ile Gly Ala Lys Thr Ser Val Ile Lys Asp His
    930                 935                 940
Asn Gly Lys Leu Phe Thr Gly Lys Asp Leu Lys Asp Ala Asn Asn Gly
945                 950                 955                 960
Ala Thr Val Ser Glu Asp Asp Gly Lys Asp Thr Gly Thr Gly Leu Val
                965                 970                 975
Thr Ala Lys Thr Val Ile Asp Ala Val Asn Lys Ser Gly Trp Arg Val
            980                 985                 990
Thr Gly Glu Gly Ala Thr Ala Glu Thr Gly Ala Thr Ala Val Asn Ala
        995                 1000                1005
Gly Asn Ala Glu Thr Val Thr Ser Gly Thr Ser Val Asn Phe Lys Asn
    1010                1015                1020
Gly Asn Ala Thr Thr Ala Thr Val Ser Lys Asp Asn Gly Asn Ile Asn
```

-continued

```
              1025                1030                1035                1040

Val Lys Tyr Asp Val Asn Val Gly Asp Gly Leu Lys Ile Gly Asp Asp
                1045                1050                1055

Lys Lys Ile Val Ala Asp Thr Thr Thr Leu Thr Val Thr Gly Gly Lys
                1060                1065                1070

Val Ser Val Pro Ala Gly Ala Asn Ser Val Asn Asn Lys Lys Leu
                1075                1080                1085

Val Asn Ala Glu Gly Leu Ala Thr Ala Leu Asn Asn Leu Ser Trp Thr
                1090                1095                1100

Ala Lys Ala Asp Lys Tyr Ala Asp Gly Glu Ser Glu Gly Glu Thr Asp
1105                1110                1115                1120

Gln Glu Val Lys Ala Gly Asp Lys Val Thr Phe Lys Ala Gly Lys Asn
                1125                1130                1135

Leu Lys Val Lys Gln Ser Glu Lys Asp Phe Thr Tyr Ser Leu Gln Asp
                1140                1145                1150

Thr Leu Thr Gly Leu Thr Ser Ile Thr Leu Gly Gly Thr Ala Asn Gly
                1155                1160                1165

Arg Asn Asp Thr Gly Thr Val Ile Asn Lys Asp Gly Leu Thr Ile Thr
                1170                1175                1180

Leu Ala Asn Gly Ala Ala Ala Gly Thr Asp Ala Ser Asn Gly Asn Thr
1185                1190                1195                1200

Ile Ser Val Thr Lys Asp Gly Ile Ser Ala Gly Asn Lys Glu Ile Thr
                1205                1210                1215

Asn Val Lys Ser Ala Leu Lys Thr Tyr Lys Asp Thr Gln Asn Thr Ala
                1220                1225                1230

Asp Glu Thr Gln Asp Lys Glu Phe His Ala Ala Val Lys Asn Ala Asn
                1235                1240                1245

Glu Val Glu Phe Val Gly Lys Asn Gly Ala Thr Val Ser Ala Lys Thr
                1250                1255                1260

Asp Asn Asn Gly Lys His Thr Val Thr Ile Asp Val Ala Glu Ala Lys
1265                1270                1275                1280

Val Gly Asp Gly Leu Glu Lys Asp Thr Asp Gly Lys Ile Lys Leu Lys
                1285                1290                1295

Val Asp Asn Thr Asp Gly Asn Asn Leu Leu Thr Val Asp Ala Thr Lys
                1300                1305                1310

Gly Ala Ser Val Ala Lys Gly Glu Phe Asn Ala Val Thr Thr Asp Ala
                1315                1320                1325

Thr Thr Ala Gln Gly Thr Asn Ala Asn Glu Arg Gly Lys Val Val Val
                1330                1335                1340

Lys Gly Ser Asn Gly Ala Thr Ala Thr Glu Thr Asp Lys Lys Val
1345                1350                1355                1360

Ala Thr Val Gly Asp Val Ala Lys Ala Ile Asn Asp Ala Thr Phe
                1365                1370                1375

Val Lys Val Glu Asn Asp Asp Ser Ala Thr Ile Asp Asp Ser Pro Thr
                1380                1385                1390

Asp Asp Gly Ala Asn Asp Ala Leu Lys Ala Xaa Asp Thr Leu Thr Leu
                1395                1400                1405

Lys Ala Gly Lys Asn Leu Lys Val Lys Arg Asp Gly Lys Asn Ile Thr
                1410                1415                1420

Phe Ala Leu Ala Asn Asp Leu Ser Val Lys Ser Ala Thr Val Ser Asp
1425                1430                1435                1440

Lys Leu Ser Leu Gly Thr Asn Gly Asn Lys Val Asn Ile Thr Ser Asp
                1445                1450                1455
```

-continued

```
Thr Lys Gly Leu Asn Phe Ala Lys Asp Ser Lys Thr Gly Asp Asp Ala
            1460                1465                1470

Asn Ile His Leu Asn Gly Ile Ala Ser Thr Leu Thr Asp Thr Leu Leu
            1475                1480                1485

Asn Ser Gly Ala Thr Thr Asn Leu Gly Gly Asn Gly Ile Thr Asp Asn
            1490                1495                1500

Glu Lys Lys Xaa Ala Ala Ser Val Lys Asp Val Leu Asn Ala Gly Trp
1505                1510                1515                1520

Asn Val Arg Gly Val Lys Pro Ala Ser Ala Asn Asn Gln Val Glu Asn
            1525                1530                1535

Ile Asp Phe Val Ala Thr Tyr Asp Thr Val Asp Phe Val Ser Gly Asp
            1540                1545                1550

Lys Asp Thr Thr Ser Val Thr Val Glu Ser Lys Asp Asn Gly Lys Arg
            1555                1560                1565

Thr Glu Val Lys Ile Gly Ala Lys Thr Ser Val Ile Lys Asp His Asn
            1570                1575                1580

Gly Lys Leu Phe Thr Gly Lys Glu Leu Lys Asp Ala Asn Asn Asn Gly
1585                1590                1595                1600

Val Thr Val Thr Glu Thr Asp Gly Lys Asp Glu Gly Asn Gly Leu Val
            1605                1610                1615

Thr Ala Lys Ala Val Ile Asp Ala Val Asn Lys Ala Gly Trp Arg Val
            1620                1625                1630

Lys Thr Thr Gly Ala Asn Gly Gln Asn Asp Asp Phe Ala Thr Val Ala
            1635                1640                1645

Ser Gly Thr Asn Val Thr Phe Ala Asp Gly Asn Gly Thr Thr Ala Glu
            1650                1655                1660

Val Thr Lys Ala Asn Asp Gly Ser Ile Thr Val Lys Tyr Asn Val Lys
1665                1670                1675                1680

Val Ala Asp Gly Leu Lys Leu Asp Gly Asp Lys Ile Val Ala Asp Thr
            1685                1690                1695

Thr Val Leu Thr Val Ala Asp Gly Lys Val Thr Ala Pro Asn Asn Gly
            1700                1705                1710

Xaa Gly Lys Lys Phe Xaa Asp Ala Ser Gly Leu Ala Gly Cys Leu Asn
            1715                1720                1725

Lys Leu Ser Xaa Thr Ala Thr Ala Gly Lys Glu Gly Thr Gly Glu Val
            1730                1735                1740

Asp Pro Ala Asn Ser Ala Gly Gln Glu Val Lys Ala Gly Asp Lys Val
1745                1750                1755                1760

Thr Phe Lys Ala Gly Asp Asn Leu Lys Ile Lys Gln Ser Xaa Lys Asp
            1765                1770                1775

Phe Thr Tyr Ser Leu Lys Lys Glu Leu Lys Asp Leu Thr Ser Val Glu
            1780                1785                1790

Phe Lys Asp Ala Asn Gly Gly Thr Gly Ser Glu Ser Thr Lys Ile Thr
            1795                1800                1805

Lys Asp Gly Leu Thr Ile Thr Pro Ala Asn Gly Ala Gly Ala Ala Gly
            1810                1815                1820

Ala Asn Thr Ala Asn Thr Ile Ser Val Thr Lys Asp Gly Ile Ser Ala
1825                1830                1835                1840

Gly Asn Lys Ala Val Thr Asn Val Val Ser Gly Leu Lys Lys Phe Gly
            1845                1850                1855

Asp Gly His Thr Leu Ala Asn Gly Thr Val Ala Asp Phe Glu Lys His
            1860                1865                1870
```

-continued

```
Tyr Asp Asn Ala Tyr Xaa Asp Leu Thr Asn Leu Asp Glu Xaa Xaa Arg
        1875                1880                1885

Ile Ile Ile Arg Leu Leu Pro Thr Ile Pro Leu Gln Pro Trp Ala Ile
        1890                1895                1900

Xaa Xaa Ala Trp Ala Gly Ser Phe
1905                1910
```

(2) INFORMATION FOR SEQ ID NO:5:

(i) SEQUENCE CHARACTERISTICS:
        (A) LENGTH: 658 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:5:

```
Met Asn Lys Ile Phe Asn Val Ile Trp Asn Val Val Thr Gln Thr Trp
1               5                   10                  15

Val Val Val Ser Glu Leu Thr Arg Thr His Thr Lys Cys Ala Ser Ala
            20                  25                  30

Thr Val Ala Val Ala Val Leu Ala Thr Leu Leu Ser Ala Thr Val Glu
        35                  40                  45

Ala Asn Asn Asn Thr Pro Val Thr Asn Lys Leu Lys Ala Tyr Gly Asp
    50                  55                  60

Ala Asn Phe Asn Phe Thr Asn Asn Ser Ile Ala Asp Ala Glu Lys Gln
65                  70                  75                  80

Val Gln Glu Ala Tyr Lys Gly Leu Leu Asn Leu Asn Glu Lys Asn Ala
                85                  90                  95

Ser Asp Lys Leu Leu Val Glu Asp Asn Thr Ala Ala Thr Val Gly Asn
            100                 105                 110

Leu Arg Lys Leu Gly Trp Val Leu Ser Ser Lys Asn Gly Thr Arg Asn
        115                 120                 125

Glu Lys Ser Gln Gln Val Lys His Ala Asp Glu Val Leu Phe Glu Gly
    130                 135                 140

Lys Gly Gly Val Gln Val Thr Ser Thr Ser Glu Asn Gly Lys His Thr
145                 150                 155                 160

Ile Thr Phe Ala Leu Ala Lys Asp Leu Gly Val Lys Thr Ala Thr Val
                165                 170                 175

Ser Asp Thr Leu Thr Ile Gly Gly Gly Ala Ala Ala Gly Ala Thr Thr
            180                 185                 190

Thr Pro Lys Val Asn Val Thr Ser Thr Thr Asp Gly Leu Lys Phe Ala
        195                 200                 205

Lys Asp Ala Ala Gly Ala Asn Gly Asp Thr Thr Val His Leu Asn Gly
    210                 215                 220

Ile Gly Ser Thr Leu Thr Asp Thr Leu Val Gly Ser Pro Ala Thr His
225                 230                 235                 240

Ile Asp Gly Gly Asp Gln Ser Thr His Tyr Thr Arg Ala Ala Ser Ile
                245                 250                 255

Lys Asp Val Leu Asn Ala Gly Trp Asn Ile Lys Gly Val Lys Ala Gly
            260                 265                 270

Ser Thr Thr Gly Gln Ser Glu Asn Val Asp Phe Val His Thr Tyr Asp
        275                 280                 285

Thr Val Glu Phe Leu Ser Ala Asp Thr Glu Thr Thr Val Thr Val
    290                 295                 300
```

```
Asp Ser Lys Glu Asn Gly Lys Arg Thr Glu Val Lys Ile Gly Ala Lys
305                 310                 315                 320

Thr Ser Val Ile Lys Glu Lys Asp Gly Lys Leu Phe Thr Gly Lys Ala
            325                 330                 335

Asn Lys Glu Thr Asn Lys Val Asp Gly Ala Asn Ala Thr Glu Asp Ala
        340                 345                 350

Asp Glu Gly Lys Gly Leu Val Thr Ala Lys Asp Val Ile Asp Ala Val
            355                 360                 365

Asn Lys Thr Gly Trp Arg Ile Lys Thr Thr Asp Ala Asn Gly Gln Asn
370                 375                 380

Gly Asp Phe Ala Thr Val Ala Ser Gly Thr Asn Val Thr Phe Ala Ser
385                 390                 395                 400

Gly Asn Gly Thr Thr Ala Thr Val Thr Asn Gly Thr Asp Gly Ile Thr
            405                 410                 415

Val Lys Tyr Asp Ala Lys Val Gly Asp Gly Leu Lys Leu Asp Gly Asp
            420                 425                 430

Lys Ile Ala Ala Asp Thr Thr Ala Leu Thr Val Asn Asp Gly Lys Asn
            435                 440                 445

Ala Asn Asn Pro Lys Gly Lys Val Ala Asp Val Ala Ser Thr Asp Glu
450                 455                 460

Lys Lys Leu Val Thr Ala Lys Gly Leu Val Thr Ala Leu Asn Ser Leu
465                 470                 475                 480

Ser Trp Thr Thr Thr Ala Ala Glu Ala Asp Gly Gly Thr Leu Asp Gly
            485                 490                 495

Asn Ala Ser Glu Gln Glu Val Lys Ala Gly Asp Lys Val Thr Phe Lys
                500                 505                 510

Ala Gly Lys Asn Leu Lys Val Lys Gln Glu Gly Ala Asn Phe Thr Tyr
            515                 520                 525

Ser Leu Gln Asp Ala Leu Thr Gly Leu Thr Ser Ile Thr Leu Gly Thr
            530                 535                 540

Gly Asn Asn Gly Ala Lys Thr Glu Ile Asn Lys Asp Gly Leu Thr Ile
545                 550                 555                 560

Thr Pro Ala Asn Gly Ala Gly Ala Asn Asn Ala Asn Thr Ile Ser Val
                565                 570                 575

Thr Lys Asp Gly Ile Ser Ala Gly Gly Gln Ser Val Lys Asn Val Val
            580                 585                 590

Ser Gly Leu Lys Lys Phe Gly Asp Ala Asn Phe Asp Pro Leu Thr Ser
            595                 600                 605

Ser Ala Asp Asn Leu Thr Lys Gln Asn Asp Asp Ala Tyr Lys Gly Leu
610                 615                 620

Thr Asn Leu Asp Glu Lys Gly Thr Asp Lys Gln Thr Pro Val Val Ala
625                 630                 635                 640

Asp Asn Thr Ala Ala Thr Val Gly Asp Leu Arg Gly Leu Gly Trp Val
                645                 650                 655

Ile Ser
```

(2) INFORMATION FOR SEQ ID NO:6:

(i) SEQUENCE CHARACTERISTICS:
        (A) LENGTH: 607 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:6:

```
Met Asn Lys Ile Phe Asn Val Ile Trp Asn Val Met Thr Gln Thr Trp
1               5                   10                  15

Val Val Val Ser Glu Leu Thr Arg Thr His Thr Lys Arg Leu Arg Asn
            20                  25                  30

Arg Gly Asp Pro Val Leu Ala Thr Leu Leu Phe Ala Thr Val Gln Ala
        35                  40                  45

Asn Ala Thr Asp Glu Asp Glu Leu Asp Pro Val Val Arg Thr Ala
50                  55                  60

Pro Val Leu Ser Phe His Ser Asp Lys Glu Gly Thr Gly Glu Lys Glu
65                  70                  75                  80

Val Thr Glu Asn Ser Asn Trp Gly Ile Tyr Phe Asp Asn Lys Gly Val
            85                  90                  95

Leu Lys Ala Gly Ala Ile Thr Leu Lys Ala Gly Asp Asn Leu Lys Xaa
            100                 105                 110

Lys Gln Xaa Thr Asp Glu Xaa Thr Asn Ala Ser Ser Phe Thr Tyr Ser
            115                 120                 125

Leu Lys Lys Asp Leu Thr Asp Leu Thr Ser Val Ala Thr Glu Lys Leu
130                 135                 140

Ser Phe Gly Ala Asn Gly Asp Lys Val Asp Ile Thr Ser Asp Ala Asn
145                 150                 155                 160

Gly Leu Lys Leu Ala Lys Thr Gly Asn Gly Asn Val His Leu Asn Gly
            165                 170                 175

Leu Asp Ser Thr Leu Pro Asp Ala Val Thr Asn Thr Gly Val Leu Ser
            180                 185                 190

Ser Ser Ser Phe Thr Pro Asn Asp Val Glu Lys Thr Arg Ala Ala Thr
            195                 200                 205

Val Lys Asp Val Leu Asn Ala Gly Trp Asn Ile Lys Gly Ala Lys Thr
210                 215                 220

Ala Gly Gly Asn Val Glu Ser Val Asp Leu Val Ser Ala Tyr Asn Asn
225                 230                 235                 240

Val Glu Phe Ile Thr Gly Asp Lys Asn Thr Leu Asp Val Val Leu Thr
            245                 250                 255

Ala Lys Glu Asn Xaa Lys Thr Thr Glu Val Lys Phe Thr Pro Lys Thr
            260                 265                 270

Ser Val Ile Lys Glu Lys Asp Gly Lys Leu Phe Thr Gly Lys Glu Asn
            275                 280                 285

Asn Asp Thr Asn Lys Val Thr Ser Asn Thr Ala Thr Asp Asn Thr Asp
290                 295                 300

Glu Gly Asn Gly Leu Val Thr Ala Lys Ala Val Ile Asp Ala Val Asn
305                 310                 315                 320

Lys Ala Gly Trp Arg Val Lys Thr Thr Thr Ala Asn Gly Gln Asn Gly
            325                 330                 335

Asp Phe Ala Thr Val Ala Ser Gly Thr Asn Val Thr Phe Glu Ser Gly
            340                 345                 350

Asp Gly Thr Thr Ala Ser Val Thr Lys Asp Thr Asn Gly Asn Gly Ile
            355                 360                 365

Thr Val Lys Tyr Asp Ala Lys Val Gly Asp Gly Leu Lys Phe Asp Ser
            370                 375                 380

Asp Lys Lys Ile Val Ala Asp Thr Thr Ala Leu Thr Val Thr Gly Gly
385                 390                 395                 400

Lys Val Ala Glu Ile Ala Lys Glu Asp Asp Lys Lys Leu Val Asn
            405                 410                 415
```

```
Ala Gly Asp Leu Val Thr Ala Leu Gly Asn Leu Ser Trp Lys Ala Lys
            420                 425                 430

Ala Glu Ala Asp Thr Asp Gly Ala Leu Glu Gly Ile Ser Lys Asp Gln
            435                 440                 445

Glu Val Lys Ala Gly Glu Thr Val Thr Phe Lys Ala Gly Lys Asn Leu
        450                 455                 460

Lys Val Lys Gln Asp Gly Ala Asn Phe Thr Tyr Ser Leu Gln Asp Ala
465                 470                 475                 480

Leu Thr Gly Leu Thr Ser Ile Thr Leu Gly Gly Thr Thr Asn Gly Gly
                485                 490                 495

Asn Asp Ala Lys Thr Val Ile Asn Lys Asp Gly Leu Thr Ile Thr Pro
            500                 505                 510

Ala Gly Asn Gly Gly Thr Thr Gly Thr Asn Thr Ile Ser Val Thr Lys
            515                 520                 525

Asp Gly Ile Lys Ala Gly Asn Lys Ala Ile Thr Asn Val Ala Ser Gly
            530                 535                 540

Leu Arg Ala Tyr Asp Asp Ala Asn Phe Asp Val Leu Asn Asn Ser Ala
545                 550                 555                 560

Thr Asp Leu Asn Arg His Val Glu Asp Ala Tyr Lys Gly Leu Leu Asn
                565                 570                 575

Leu Asn Glu Lys Asn Ala Asn Lys Gln Pro Leu Val Thr Asp Ser Thr
            580                 585                 590

Ala Ala Thr Val Gly Asp Leu Arg Lys Leu Gly Trp Val Val Ser
            595                 600                 605
```

HAEMOPHILUS ADHESION PROTEINS

This is a division of application Ser. No. 08/409,995 filed Mar. 24, 1995, U.S. Pat. No. 5,646,259.

The U.S. Government has certain rights in this invention pursuant to grant nos. AI-21707 and HD-29687 from the National Institutes of Health.

FIELD OF THE INVENTION

The invention relates to novel Haemophilus adhesion proteins, nucleic acids, and antibodies.

BACKGROUND OF THE INVENTION

Most bacterial diseases begin with colonization of a particular mucosal surface (Beachey et al., 1981, J. Infect. Dis. 143:325–345). Successful colonization requires that an organism overcome mechanical cleansing of the mucosal surface and evade the local immune response. The process of colonization is dependent upon specialized microbial factors that promote binding to host cells (Hultgren et al., 1993 Cell, 73:887–901). In some cases the colonizing organism will subsequently enter (invade) these cells and survive intracellularly (Falkow, 1991, Cell 65:1099–1102).

Haemophilus influenzae is a common commensal organism of the human respiratory tract (Kuklinska and Kilian, 1984, Eur. J. Clin. Microbiol. 3:249–252). It is the most common cause of bacterial meningitis and a leading cause of other invasive (bacteraemic) diseases. In addition, this organism is responsible for a sizeable fraction of acute and chronic otitis media, sinusitis, bronchitis, and pneumonia.

Haemophilus influenzae is a human-specific organism that normally resides in the human nasopharynx and must colonize this site in order to avoid extinction. This microbe has a number of surface structures capable of promoting attachment to host cells (Guerina et al., 1982, J. Infect Dis. 146:564; Pichichero et al., 1982, Lancet ii:960–962; St Geme et al., 1993, Proc. Natl. Acad. Sci. U.S.A. 90:2875–2879). In addition, H. influenzae has acquired the capacity to enter and survive within these cells (Forsgren et al., 1994, Infect. Immun. 62:673–679; St Geme and Falkow, 1990, Infect. Immun. 58:4036–4044; St. Geme and Falkow, 1991, Infect. Immun. 59:1325–1333, Infect. Immun. 59:3366–3371). As a result, this bacterium is an important cause of both localized respiratory tract and systemic disease (Turk, 1984, J. Med. Microbiol. 18:1–16). Nonencapsulated, non-typable strains account for the majority of local disease (Turk, 1984, supra); in contrast, serotype b strains, which express a capsule composed of a polymer of ribose and ribitol-5-phosphate (PRP), are responsible for over 95% of cases of H. influenzae systemic disease (Turk, 1982, Clinical importance of Haemophilus influenzae, p. 3–9. In S. H. Sell and P. F. Wright (ed.), Haemophilus influenzae epidemiology, immunology, and prevention of disease. Elsevier/North-Holland Publishing Co., New York).

The initial step in the pathogenesis of disease due to H. influenzae involves colonization of the upper respiratory mucosa (Murphy et al., 1987, J. Infect. Dis. 5:723–731). Colonization with a particular strain may persist for weeks to months, and most individuals remain asymptomatic throughout this period (Spinola et al., 1986, I. Infect. Dis. 154:100–109). However, in certain circumstances colonization will be followed by contiguous spread within the respiratory tract, resulting in local disease in the middle ear, the sinuses, the conjunctiva, or the lungs. Alternatively, on occasion bacteria will penetrate the nasopharyngeal epithelial barrier and enter the bloodstream.

In vitro observations and animal studies suggest that bacterial surface appendages called pili (or fimbriae) play an important role in H. influenzae colonization. In 1982 two groups reported a correlation between piliation and increased attachment to human oropharyngeal epithelial cells and erythrocytes (Guerina et al., supra; Pichichero et al., supra). Other investigators have demonstrated that anti-pilus antibodies block in vitro attachment by piliated H. influenzae (Forney et al., 1992, J. Infect. Dis. 165:464–470; van Alphen et al., 1988, Infect. Immun. 56:1800–1806). Recently Weber et al. insertionally inactivated the pilus structural gene in an H. influenzae type b strain and thereby eliminated expression of pili; the resulting mutant exhibited a reduced capacity for colonization of year-old monkeys (Weber et al., 1991, Infect. Immun. 59:4724–4728).

A number of reports suggest that nonpilus factors also facilitate Haemophilus colonization. Using the human nasopharyngeal organ culture model, Farley et al. (1986, J. Infect. Dis. 161:274–280) and Loeb et al. (1988, Infect. Immun. 49:484–489) noted that nonpiliated type b strains were capable of mucosal attachment. Read and coworkers made similar observations upon examining nontypable strains in a model that employs nasal turbinate tissue in organ culture (1991, J. Infect Dis. 163:549–558). In the monkey colonization study by Weber et al. (1991, supra), nonpiliated organisms retained a capacity for colonization, though at reduced densities; moreover, among monkeys originally infected with the piliated strain, virtually all organisms recovered from the nasopharynx were nonpiliated. All of these observations are consistent with the finding that nasopharyngeal isolates from children colonized with H. influenzae are frequently nonpiliated (Mason et al., 1985, Infect. Immun. 49:98–103; Brinton et al., 1989, Pediatr. Infect. Dis. J. 8:554–561).

Previous studies have shown that H. influenzae are capable of entering (invading) cultured human epithelial cells via a pili-independent mechanism (St. Geme and Falkow, 1990, supra; St. Geme and Falkow, 1991, supra). Although H. influenzae is not generally considered an intracellular parasite, a recent report suggests that these in vitro findings may have an in vivo correlate (Forsgren et al., 1994, supra). Forsgren and coworkers examined adenoids from 10 children who had their adenoids removed because of long-standing secretory otitis media or adenoidal hypertrophy. In all 10 cases there were viable intracellular H. influenzae. Electron microscopy demonstrated that these organisms were concentrated in the reticular crypt epithelium and in macrophage-like cells in the subepithelial layer of tissue. One possibility is that bacterial entry into host cells provides a mechanism for evasion of the local immune response, thereby allowing persistence in the respiratory tract.

Thus, a vaccine for the therapeutic and prophylactic treatment of Haemophilus infection is desirable. Accordingly, it is an object of the present invention to provide for recombinant Haemophilus Adherence (HA) proteins and variants thereof, and to produce useful quantities of these HA proteins using recombinant DNA techniques.

It is a further object of the invention to provide recombinant nucleic acids encoding HA proteins, and expression vectors and host cells containing the nucleic acid encoding the HA protein.

An additional object of the invention is to provide monoclonal antibodies for the diagnosis of Haemophilus infection.

A further object of the invention is to provide methods for producing the HA proteins, and a vaccine comprising the HA proteins of the present invention. Methods for the therapeutic and prophylactic treatment of Haemophilus infection are also provided.

SUMMARY OF THE INVENTION

In accordance with the foregoing objects, the present invention provides recombinant HA proteins, and isolated or recombinant nucleic acids which encode the HA proteins of the present invention. Also provided are expression vectors which comprise DNA encoding a HA protein operably linked to transcriptional and translational regulatory DNA, and host cells which contain the expression vectors.

The invention provides also provides methods for producing HA proteins which comprises culturing a host cell transformed with an expression vector and causing expression of the nucleic acid encoding the HA protein to produce a recombinant HA protein.

The invention also includes vaccines for *Haemophilus influenzae* infection comprising an HA protein for prophylactic or therapeutic use in generating an immune response in a patient. Methods of treating or preventing *Haemophilus influenzae* infection comprise administering a vaccine.

BRIEF DESCRIPTION OF THE DRAWINGS

FIGS. 1A and 1B depict the nucleic acid sequence (SEQ ID NO: 1) of HA1.

FIGS. 2A–2D depict the amino acid sequence (SEQ ID NO: 2) of HA1.

FIGS. 3A, 3B, 3C and 3D depict the nucleic acid sequence (SEQ ID NO: 3) of HA2.

FIGS. 4A–4D depict the amino acid sequence (SEQ ID NO: 4) of HA2.

FIG 5 (SEQ ID NOS: 5–6) depicts the homology between the N-terminal amino acid sequences of HA1 and HA2. Single letters abbreviations are used for the amino acids. A line indicates identity between residues, and two dots indicate conservative changes, i.e. similarity between residues.

FIG. 6 depicts the restriction maps of phage 11-17 and plasmid pT7-7 subclones.

DETAILED DESCRIPTION OF THE INVENTION

The present invention provides novel Haemophilus Adhesion (HA) proteins. In a preferred embodiment, the HA proteins are from Haemophilus strains, and in the preferred embodiment, from *Haemophilus influenza*. In particular, *H. influenzae* encapsulated type b strains are used to clone the HA proteins of the invention. However, using the techniques outlined below, HA proteins from other *Haemophilus influenzae* strains, or from other bacterial species such as Neisseria spp. or Bordetalla spp. may also be obtained.

Two HA proteins, HA1 and HA2, are depicted in FIGS. 2 and 4 (SEQ ID NOS: 2 and 4). HA2 is associated with the formation of surface fibrils, which are involved in adhesion to various host cells. HA1 has also been implicated in adhesion to a similar set of host cells. When the HA1 nucleic acid (SEQ ID NO: 1) is expressed in a non-adherent strain of *E. coli* as described below, the *E. coli* acquire the ability to adhere to human host cells.

A HA protein may be identified in several ways. A HA nucleic acid or HA protein is initially identified by substantial nucleic acid and/or amino acid sequence homology to the sequences shown in FIGS. 1–4 (SEQ ID NOS: 1–4). Such homology can be based upon the overall nucleic acid or amino acid sequence.

As used herein, a protein is a "HA protein" if the overall homology of the protein sequence to the amino acid sequence shown in FIGS. 2 and 4 (SEQ ID NOS: 2 and 4) is preferably greater than about 50%, more preferably greater than about 65% and most preferably greater than 80%. In some embodiments the homology will be as high as about 90 to 95 or 98%. This homology will be determined using standard techniques known in the art, such as the Best Fit sequence program described by Devereux et al., *Nucl. Acid Res.* 12:387–395 (1984). The alignment may include the introduction of gaps in the sequences to be aligned. As noted below, in the comparison of proteins of different lengths, such as HA1 and HA2, the homology is determined on the basis of the length of the shorter sequence.

In a preferred embodiment, a HA protein is defined as having homology to the homologous unique N-terminal region of HA1 and HA2 depicted in FIG. 5 (SEQ ID NOS: 5 and 6). The homology to the N-terminal region, comprising approximately the first 650 amino acids of the proteins, is preferably greater than about 50%, more preferably greater than about 65% and most preferably greater than 80%. In some embodiments the homology will be as high as about 90 to 95 or 98%. It is preferred that this unique N-terminal region be used to identify a HA protein.

The HA proteins of the present invention have limited homology to the high molecular weight protein-1 (HMW1) of *H. influenzae*, as well as the AIDA-I adhesion of *E. coli*. For the HMW1 protein, this homology is greatest between residues 60–540 of the HA1 protein and residues 1100 to about 1550 of HMW1, with 20% homology in this overlap region. For the AIDA-I protein, there is a roughly 50% homology between the first 30 amino acids of AIDA-I and HA1, and the overall homology between the proteins is roughly 22%.

In addition, the N-termini of the HA1 and HA2 proteins of the present invention have homology to each other, as shown in FIG. 5 (SEQ ID NOS: 5 and 6). This homology is roughly 59% over the first 650 amino acids. Thus, for the purposes of the invention, HA1 and HA2 are both HA proteins.

An "HA1" protein is defined by substantial homology to the sequence shown in FIG. 2 (SEQ ID NO: 2). This homology is preferably greater than about 60%, more preferably greater than about 70% and most preferably greater than 80%. In preferred embodiments the homology will be as high as about 90 to 95 or 98%. In addition, HA1 proteins may be defined by substantial homology to the C-terminal portion of the sequence shown in FIG. 2, which is not homologous to the HA2 sequence. C-terminal homology will be greater than about 50%, preferably greater than about 75%, and most preferably greater than about 90%. Similarly, an "HA2" protein may be defined by substantial homology to the sequence shown in FIG. 3 (SEQ ID NO: 3), as defined above, and more preferably by substantial homology to the C-terminal portion of the sequence shown in FIG. 3 (SEQ ID NO: 3), as defined above.

In addition, for sequences which contain either more or fewer amino acids than the proteins shown in FIGS. 2 and 4 (SEQ ID NOS: 2 and 4), it is understood that the percentage of homology will be determined based on the number of homologous amino acids in relation to the total number of amino acids. Thus, for example, homology of sequences shorter than that shown in FIGS. 2 and 4 (SEQ ID NOS: 2 and 4), as discussed below, will be determined using the number of amino acids in the shorter sequence.

HA proteins of the present invention may be shorter than the amino acid sequences shown in FIGS. 2 and 4 (SEQ ID NOS: 2 and 4). Thus, in a preferred embodiment, included within the definition of HA proteins are portions or fragments of the sequence shown in FIGS. 2 and 4 (SEQ ID NOS: 2 and 4). Generally, the HA protein fragments may range in size from about 7 amino acids to about 800 amino acids, with from about 15 to about 700 amino acids being preferred, and from about 100 to about 650 amino acids also preferred. Particularly preferred fragments are sequences unique to HA; these sequences have particular use in cloning HA proteins from other organisms, to generate antibodies specific to HA proteins, or for particular use as a vaccine. Unique sequences are easily identified by those skilled in the art after examination of the HA protein sequence and comparison to other proteins; for example, by examination of the sequence alignment shown in FIGS. 2 and 4 (SEQ ID NOS: 2 and 4). Preferred unique sequences include the N-terminal region of the HA1 and HA2 sequences, comprising roughly 650 amino acids, depicted in FIGS. 2 and 4 (SEQ ID NOS: 2 and 4). HA protein fragments which are included within the definition of a HA protein include N- or C-terminal truncations and deletions which still allow the protein to be biologically active; for example, which still allow adherence, as described below. In addition, when the HA protein is to be used to generate antibodies, for example as a vaccine, the HA protein must share at least one epitope or determinant with the sequences shown in FIGS. 2 and 4 (SEQ ID NOS: 2 and 4). In a preferred embodiment, the epitope is unique to the HA protein; that is, antibodies generated to a unique epitope exhibit little or no cross-reactivity with other proteins. However, cross reactivity with other proteins does not preclude such epitopes or antibodies for immunogenic or diagnostic uses. By "epitope" or "determinant" herein is meant a portion of a protein which will generate and/or bind an antibody. Thus, in most instances, antibodies made to a smaller HA protein will be able to bind to the full length protein.

In some embodiments, the fragment of the HA protein used to generate antibodies are small; thus, they may be used as haptens and coupled to protein carries to generate antibodies, as is known in the art.

In addition, sequences longer than those shown in FIGS. 2 and 4 (SEQ ID NOS: 2 and 4) are also included within the definition of HA proteins. In particular, the nucleic acid and amino acid sequences shown in FIGS. 3 and 4 (SEQ ID NOS: 3 and 4) for HA2 represent a portion of the full-length sequence. It is estimated that the HA2 protein extends for another 350 or so amino acids.

Preferably, the antibodies are generated to a portion of the HA protein which is exposed at the outer membrane, i.e. surface exposed. The amino-terminal portions of HA1 and HA2 are believed to be externally exposed proteins.

In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence. Thus the homology of the nucleic acid sequence as compared to the nucleic acid sequences of FIGS. 1 and 3 (SEQ ID NOS: 1 and 3) is preferably greater than about 40%, more preferably greater than about 60% and most preferably greater than 80%. In some embodiments the homology will be as high as about 90 to 95 or 98%.

As outlined for the protein sequences, a preferred embodiment utilizes HA nucleic acids with substantial homology to the unique N-terminal region of the HA1 and HA2 depicted in FIG. 5 (SEQ ID NOS: 5 and 6).

In one embodiment, the nucleic acid homology is determined through hybridization studies. Thus, for example, nucleic acids which hybridize under high stringency to all or part of the nucleic acid sequences shown in FIGS. 1 and 3 (SEQ ID NOS: 1 and 3) are considered HA protein genes. High stringency conditions include washes with 0.1×SSC at 65° C. for 2 hours.

The HA proteins and nucleic acids of the present invention are preferably recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Specifically included within the definition of nucleic acid are anti-sense nucleic acids. An anti-sense nucleic acid will hybridize to the corresponding non-coding strand of the nucleic acid sequences shown in FIGS. 1 and 3 (SEQ ID NOS: 1 and 3), but may contain ribonucleotides as well as deoxyribonucleotides. Generally, anti-sense nucleic acids function to prevent expression of mRNA, such that a HA protein is not made, or made at reduced levels. The nucleic acid may be double stranded, single stranded, or contain portions of both double stranded or single stranded sequence. By the term "recombinant nucleic acid" herein is meant nucleic acid, originally formed in vitro by the manipulation of nucleic acid by endonucleases, in a form not normally found in nature. Thus an isolated HA protein gene, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated away from some or all of the proteins and compounds with which it is normally associated in its wild type host, or found in the absence of the host cells themselves. Thus, the protein may be partially or substantially purified. The definition includes the production of a HA protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions. Furthermore, although not normally considered "recombinant", proteins or portions of proteins which are synthesized chemically, using the sequence information of FIGS. 2 and 4 (SEQ ID NOS: 2 and 4), are considered recombinant herein as well.

Also included with the definition of HA protein are HA proteins from other organisms, which are cloned and expressed as outlined below.

In the case of anti-sense nucleic acids, an anti-sense nucleic acid is defined as one which will hybridize to all or part of the corresponding non-coding sequence of the sequences shown in FIGS. 1 and 3 (SEQ ID NOS: 1 and 3). Generally, the hybridization conditions used for the determination of anti-sense hybridization will be high stringency conditions, such as 0.1×SSC at 65° C.

Once the HA protein nucleic acid is identified, it can be cloned and, if necessary, its constituent parts recombined to form the entire HA protein nucleic acid. Once isolated from its natural source, e.g., contained within a plasmid or other vector or excised therefrom as a linear nucleic acid segment, the recombinant HA protein nucleic acid can be further used as a probe to identify and isolate other HA protein nucleic acids. It can also be used as a "precursor" nucleic acid to make modified or variant HA protein nucleic acids and proteins.

Using the nucleic acids of the present invention which encode HA protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the HA protein. "Operably linked" in this context means that the transcriptional and translational regulatory DNA is positioned relative to the coding sequence of the HA protein in such a manner that transcription is initiated. Generally, this will mean that the promoter and transcriptional initiation or start sequences are positioned 5' to the HA protein coding region. The transcriptional and translational regulatory nucleic acid will generally be appropriate to the host cell used to express the HA protein; for example, transcriptional and translational regulatory nucleic acid sequences from Bacillus will be used to express the HA protein in Bacillus. Numerous types of appropriate expression vectors, and suitable regulatory sequences are known in the art for a variety of host cells.

In general, the transcriptional and translational regulatory sequences may include, but are not limited to, promoter sequences, leader or signal sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The HA proteins of the present invention are produced by culturing a host cell transformed with an expression vector containing nucleic acid encoding a HA protein, under the appropriate conditions to induce or cause expression of the HA protein. The conditions appropriate for HA protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis*, SF9 cells, C129 cells, 293 cells, Neurospora, BHK, CHO, COS, and HeLa cells, immortalized mammalian myeloid and lymphoid cell lines.

In a preferred embodiment, HA proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of HA protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the HA protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, HA proteins are produced in insect cells. Expression vectors for the transformation of insect cells, and in particular, baculovirus-based expression vectors, are well known in the art. Briefly, baculovirus is a very large DNA virus which produces its coat protein at very high levels. Due to the size of the baculoviral genome, exogenous genes must be placed in the viral genome by recombination. Accordingly, the components of the expression system include: a transfer vector, usually a bacterial plasmid, which contains both a fragment of the baculovirus genome, and a convenient restriction site for insertion of the HA protein; a wild type baculovirus with a sequence homologous to the baculovirus-specific fragment in the transfer vector (this allows for the homologous recombination of the heterologous gene into the baculovirus genome); and appropriate insect host cells and growth media.

Mammalian expression systems are also known in the art and are used in one embodiment. A mammalian promoter is any DNA sequence capable of binding mammalian RNA polymerase and initiating the downstream (3') transcription of a coding sequence for HA protein into mRNA. A promoter will have a transcription initiating region, which is usuallyy place proximal to the 5' end of the coding sequence, and a TATA box, using a located 25–30 base pairs upstream of the transcription initiation site. The TATA box is though to direct RNA polymerase II to begin RNA synthesis at the correct site. A mammalian promoter will also contain an upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, and herpes simplex virus promoter.

Typically, transcription termination and polyadenylation sequences recognized by mammalian cells are regulatory regions located 3+ to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, encapsulation of the polynucleotide (s) in liposomes, and direct microinjection of the DNA into nuclei.

In a preferred embodiment, HA protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the G418 resistance gene, which confers resistance to G418; and the CUP1 gene, which allows yeast to grow in the presence of copper ions.

A recombinant HA protein may be expressed intracellularly or secreted. The HA protein may also be made as a fusion protein, using techniques well known in the art. Thus, for example, if the desired epitope is small, the HA protein may be fused to a carrier protein to form an immunogen. Alternatively, the HA protein may be made as a fusion protein to increase expression.

Also included within the definition of HA proteins of the present invention are amino acid sequence variants. These variants fall into one or more of three classes: substitutional, insertional or deletional variants. These variants ordinarily are prepared by site specific mutagenesis of nucleotides in the DNA encoding the HA protein, using cassette mutagenesis or other techniques well known in the art, to produce DNA encoding the variant, and thereafter expressing the DNA in recombinant cell culture as outlined above. However, variant HA protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the HA protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed HA protein variants screened for the optimal combination of desired activity. Techniques for making substitution mutations at predetermined sites in DNA having a known sequence are well known, for example, M13 primer mutagenesis. Screening of the mutants is done using assays of HA protein activities; for example, mutated HA genes are placed in HA deletion strains and tested for HA activity, as disclosed herein. The creation of deletion strains, given a gene sequence, is known in the art. For example, nucleic acid encoding the variants may be expressed in an adhesion deficient strain, and the adhesion and infectivity of the variant *Haemophilus influenzae* evaluated. For example, as outlined below, the variants may be expressed in the *E. coli* DH5α non-adherent strain, and the transformed *E. coli* strain evaluated for adherence using Change conjunctival cells.

Amino acid substitutions are typically of single residues; insertions usually will be on the order of from about 1 to 20 amino acids, although considerably larger insertions may be tolerated. Deletions range from about 1 to 30 residues, although in some cases deletions may be much larger, as for example when one of the domains of the HA protein is deleted.

Substitutions, deletions, insertions or any combination thereof may be used to arrive at a final derivative. Generally these changes are done on a few amino acids to minimize the alteration of the molecule. However, larger changes may be tolerated in certain circumstances.

When small alterations in the characteristics of the HA protein are desired, substitutions are generally made in accordance with the following chart:

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the polypeptide as needed. Alternatively, the variant may be designed such that the biological activity of the HA protein is altered.

In a preferred embodiment, the HA protein is purified or isolated after expression. HA proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the HA protein may be purified using a standard anti-HA antibody column. Ultrafiltration and diafiltration techniques, in conjunction with protein concentration, are also useful. For general guidance in suitable purification techniques, see Scopes, R., Protein Purification, Springer-Verlag, New York (1982). The degree of purification necessary will vary depending on the use of the HA protein. In some instances no purification will be necessary.

Once expressed and purified if necessary, the HA proteins are useful in a number of applications.

For example, the HA proteins can be coupled, using standard technology, to affinity chromatography columns. These columns may then be used to purify antibodies from samples obtained from animals or patients exposed to the *Haemophilus influenzae* organism. The purified antibodies may then be used as outlined below.

Additionally, the HA proteins are useful to make antibodies to HA proteins. These antibodies find use in a number of applications. The antibodies are used to diagnose the presence of an *Haemophilus influenzae* infection in a sample or patient. In a preferred embodiment, the antibodies are used to detect the presence of nontypable *Haemophilus influenza* (NTHI), although typable *H influenzae* infections are also detected using the antibodies.

This diagnosis will be done using techniques well known in the art; for example, samples such as blood or tissue samples may be obtained from a patient and tested for reactivity with the antibodies, for example using standard techniques such as ELISA. In a preferred embodiment, monoclonal antibodies are generated to the HA protein, using techniques well known in the art. As outlined above, the antibodies may be generated to the full length HA protein, or a portion of the HA protein.

Antibodies generated to HA proteins may also be used in passive immunization treatments, as is known in the art.

Antibodies generated to unique sequences of HA proteins may also be used to screen expression libraries from other organisms to find, and subsequently clone, HA nucleic acids from other organisms.

In one embodiment, the antibodies may be directly or indirectly labelled. By "labelled" herein is meant a compound that has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position. Thus, for example, the HA protein antibody may be labelled for detection, or a secondary antibody to the HA protein antibody may be created and labelled.

In one embodiment, the antibodies generated to the HA proteins of the present invention are used to purify or separate HA proteins or the *Haemophilus influenzae* organism from a sample. Thus for example, antibodies generated to HA proteins which will bind to the *Haemophilus influenzae* organism may be coupled, using standard technology, to affinity chromatography columns. These columns can be used to pull out the Haemophilus organism from environmental or tissue samples.

In a preferred embodiment, the HA proteins of the present invention are used as vaccines for the prophylactic or therapeutic treatment of a *Haemophilus influenzae* infection in a patient. By "vaccine" or "immunogenic compositions" herein is meant an antigen or compound which elicits an immune response in an animal or patient. The vaccine may be administered prophylactically, for example to a patient never previously exposed to the antigen, such that subsequent infection by the *Haemophilus influenzae* organism is prevented. Alternatively, the vaccine may be administered therapeutically to a patient previously exposed or infected by the *Haemophilus influenzae* organism. While infection cannot be prevented, in this case an immune response is generated which allows the patient's immune system to more effectively combat the infection. Thus, for example, there may be a decrease or lessening of the symptoms associated with infection.

A "patient" for the purposes of the present invention includes both humans and other animals and organisms. Thus the methods are applicable to both human therapy and veterinary applications.

The administration of the HA protein as a vaccine is done in a variety of ways. Generally, the HA proteins can be formulated according to known methods to prepare pharmaceutically useful compositions, whereby therapeutically effective amounts of the HA protein are combined in admixture with a pharmaceutically acceptable carrier vehicle. Suitable vehicles and their formulation are well known in the art. Such compositions will contain an effective amount of the HA protein together with a suitable amount of vehicle in order to prepare pharmaceutically acceptable compositions for effective administration to the host. The composition may include salts, buffers, carrier proteins such as serum albumin, targeting molecules to localize the HA protein at the appropriate site or tissue within the organism, and other molecules. The composition may include adjuvants as well.

In one embodiment, the vaccine is administered as a single dose; that is, one dose is adequate to induce a sufficient immune response to prophylactically or therapeutically treat a *Haemophilus influenzae* infection. In alternate embodiments, the vaccine is administered as several doses over a period of time, as a primary vaccination and "booster" vaccinations.

By "therapeutically effective amounts" herein is meant an amount of the HA protein which is sufficient to induce an immune response. This amount may be different depending on whether prophylactic or therapeutic treatment is desired. Generally, this ranges from about 0.001 mg to about 1 gm, with a preferred range of about 0.05 to about 0.5 gm. These amounts may be adjusted if adjuvants are used.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are specifically incorporated by reference.

EXAMPLE

Cloning of HA1

Many protocols are substantially the same as those outlined in St. Geme et al., Mol. Microbio. 15(1):77–85 (1995).
Bacterial Strains, Plasmids, and Phages Nontypable *H. influenzae* strain 11 was the clinical isolate chosen as a prototypic HMW1/HMW2-non-expressing strain, although a variety of encapsulated typable strains can be used to clone the protein using the sequences of the figures. The organism was isolated in pure culture from the middle ear fluid of a child with acute otitis media. The strain was identified as *H. influenzae* by standard methods and was classified as nontypable by its failure to agglutinate with a panel of typing antisera for *H. influenzae* types a to f (Burroughs Wellcome Co., Research Triangle Park, North Carolina) and failure to show lines of precipitation with these antisera in counterimmunoelectrophoresis assays. Strain 11 adheres efficiently to Chang conjunctival cells in vitro, at levels comparable to those previously demonstrated for NTHI strains expressing HMW1/HMW2-like proteins (data not shown). Convalescent serum from the child infected with this strain demonstrated an antibody response directed predominantly against surface-exposed high molecular weight proteins with molecular weights greater than 100 kDa.

M13mp18 and M13mp19 were obtained from New England BioLabs, Inc. (Beverly, Mass.) pT7-7 was the kind gift of Stanley Tabor. This vector contains the T7 RNA polymerase promoter φ10, a ribosome-binding site, and the translational start site for the T7 gene 10 protein upstream from a multiple cloning site.
Molecular Coning and Plasmid Subcloning The recombinant phage containing the HA1 gene was isolated and characterized using methods similar to those described previously. In brief, chromosomal DNA from strain 11 was prepared and Sau3A partial restriction digests of the DNA were prepared and fractionated on 0.7% agarose gels. Fractions containing DNA fragments in the 9- to 20-kbp range were pooled, and a library was prepared by ligation into λEMBL3 arms. Ligation mixtures were packaged in vitro with Gigapack (Stratagene) and plate-amplified in a P2 lysogen of *E. coli* LE392. Lambda plaque immunological screening was performed as described by Maniatis et al., Molecular Cloning: A Laboratory Manual, 2d Ed. (1989), Cold Spring Harbor Press. For plasmid subcloning studies, DNA from recombinant phage was subcloned into the T7 expression plasmid pT7-7. Standard methods were used for manipulation of cloned DNA as described by Maniatis et al (supra).

Plasmid pHMW8-3 was generated by isolating an 11 kbp Xbal fragment from purified DNA from recombinant phage clone 11-17 and ligating into Xbal cut pT7-7. Plasmid pHMW8-4 was generated by isolating a 10 kbp BamHI-Cia1 cut pT7-7. Plasmid pHMW8-5 was generated by digesting plasmid pHMW8-3 DNA with Cla1, isolating the larger fragment and religating. Plasmid pHMW8-6 was generated by digesting pHMW8-4 with Spe1, which cuts at a unique site within the HA1 gene, blunt-ending the resulting fragment, inserting a kanamycin resistance cassette into the Spe1 site. Plasmid pHMW8-7 was generated by digesting pHMW8-3 with NruI and HindIII, isolating the fragment containing pT7-7, blunt-ending and religating. The plasmid restriction maps are shown in FIG. 6.
DNA Sequence Analysis DNA sequence analysis was performed by the dideoxy method with the U.S. Biochemicals Sequenase kit as suggested by the manufacturer. [$^{36}$S]dATP was purchased from New England Nuclear (Boston, Mass). Data were analyzed with Compugene software and the Genetics Computer Group program from the University of Wisconsin on a Digital VAX 8530 computer. Several 21-mer oligonucleotide primers were generated as necessary to complete the sequence.
Adherence Assays Adherence assays were done with Chang epithelial cells [Wong-Kilbourne derivative, clone 1-5c-4 (human conjunctiva), ATCC CCL20.2)], which were seeded into wells of 24-well tissue culture plates, as described (St. Geme III et al., Infect. Immun. 58:4036 (1990)). Bacteria were inoculated into broth and allowed to grow to a density of approximately $2 \times 10^9$ colony-forming units per ml. Approximately $2 \times 10^7$ colony-forming units were inoculated onto epithelial cells monolayers, and plates were gently centrifuged at 165×g for 5 min to facilitate contact between bacteria and the epithelial surface. After incubation for 30 min at 37° C. in 5% $CO_2$, monolayers were rinsed five times with phosphate buffered saline (PBS) to remove nonadherent organisms and were treated with trypsin-EDTA (0.05% trypsin/0.5% EDTA) in PBS to release them from the plastic support. Well contents were agitated, and dilution were plated on solid medium to yield the number of adherent bacteria per monolayer. Percent adherence we calculated by dividing the number of adherent colony-forming units per monolayer by the number of inoculated colony-forming units.

Isolation and Characterization of Recombinant Phage Expressing the Strain 11 High Molecular Weight Adhesion Protein The nontypable *Haemophilus influenzae* strain 11 chromosomal DNA library was screened immunologically with convalescent serum from the child infected with strain 11. Immunoreactive clones were screened by Western blot for expression of high molecular weight proteins with apparent molecular weights >100 kDa and two different classes of recombinant clones were recovered. A single clone designated 11-17 was recovered which expressed the HA1 protein. The recombinant protein expressed by this clone had an apparent molecular weight of greater than 200 kDa Transformation into *E. coli*

Plasmids were introduced into DH5α strain of *E. coli* (Maniatis, supra), which is a non-adherent strain, using electroporation (Dower et al., Nucl. Acids Res. 16:6127 (1988). The results are shown in Table 1.

TABLE 1

| Strain | % Adherence* |
| --- | --- |
| DH5α(pHMW 8-4) | 43.3 ± 5.0% |
| DH5α(pHMW 8-5) | 41.3 ± 3.3% |
| DH5α(pHMW 8-6) | 0.6 ± 0.3% |
| DH5α(pHMW 8-7) | |
| DH5α(pT7-7) | 0.4 ± 0.1% |

*Adherence was measured in a 30 minute assay and was calculated by dividing the number of adherent bacteria by the number of inoculated bacteria. Values are the mean ± SEM of measurements made in triplicate from a representative experiment.

In addition, a monoclonal antibody made by standard procedures, directed against the strain 11 protein recognized proteins in 57 of 60 epidemiologically-unrelated NTHI. However, Southern analysis using the gene indicated that roughly only 25% of the tested strains actually hybridized to the gene (data not shown).

We claim:

1. A recombinant Haemophilus adhesion protein having the sequence shown in FIG. 2 (SEQ ID NO:2).

2. A recombinant Haemophilus adhesion protein having the sequence shown in FIG. 4 (SEQ ID NO:4).

3. A recombinant Haemophilus adhesion protein encoded by a nucleic acid which will hybridize under high stringency conditions to the nucleic acid shown in FIG. 1 (SEQ ID NO:1).

4. A recombinant Haemophilus adhesion protein encoded by a nucleic acid which will hybridize under high stringency conditions to the nucleic acid shown in FIG. 3 (SEQ ID NO:3).

* * * * *